US009925036B2

United States Patent
Heaven et al.

(10) Patent No.: US 9,925,036 B2
(45) Date of Patent: Mar. 27, 2018

(54) SYSTEM AND METHOD FOR SECURING TISSUE TO BONE

(71) Applicant: Conmed Corporation, Utica, NY (US)

(72) Inventors: Malcolm Heaven, Reno, NV (US);
John P. Greelis, Carlsbad, CA (US);
Mikxay Sirivong, Escondido, CA (US);
Matthew T. Yurek, San Diego, CA (US)

(73) Assignee: Conmed Corporation, Utica, NY (US)

( * ) Notice: Subject to any disclaimer, the term of this patent is extended or adjusted under 35 U.S.C. 154(b) by 75 days.

(21) Appl. No.: 14/774,663

(22) PCT Filed: Mar. 7, 2014

(86) PCT No.: PCT/US2014/022014
§ 371 (c)(1),
(2) Date: Sep. 10, 2015

(87) PCT Pub. No.: WO2014/150053
PCT Pub. Date: Sep. 25, 2014

(65) Prior Publication Data
US 2016/0038274 A1    Feb. 11, 2016

Related U.S. Application Data

(60) Provisional application No. 61/801,255, filed on Mar. 15, 2013.

(51) Int. Cl.
*A61F 2/08*     (2006.01)
*A61B 17/04*    (2006.01)

(52) U.S. Cl.
CPC ........ *A61F 2/0811* (2013.01); *A61B 17/0401* (2013.01); *A61B 2017/0403* (2013.01);
(Continued)

(58) Field of Classification Search
CPC ............ A61F 2/0811; A61F 2002/0829; A61F 2002/0864; A61F 2002/0835
See application file for complete search history.

(56) References Cited

U.S. PATENT DOCUMENTS 4,590,928 A   5/1986   Hunt et al.
4,738,255 A   4/1988   Goble et al.
(Continued)

FOREIGN PATENT DOCUMENTS

EP   0241240   10/1987
EP   0270704   6/1988
(Continued)

OTHER PUBLICATIONS

Extended European Search Report dated Feb. 27, 2017, PCT/US2014/022014; 10 pages.
(Continued)

*Primary Examiner* — Thomas J Sweet
*Assistant Examiner* — Daniel Bissing
(74) *Attorney, Agent, or Firm* — Frederick J M Price; Bond, Schoeneck & King, PLLC

(57) ABSTRACT

Disclosed herein are methods and devices for securing soft tissue to a rigid material such as bone. A tissue anchoring device is described that comprises an anchor body and a spreader such that tissue may be captured or compressed between outside surfaces on the anchor and inside surfaces of a bone tunnel to secure the tissue within the tunnel. Methods are described that enable use of the bone anchoring device to secure a tissue graft into the tibial and femoral bones during anterior cruciate ligament ("ACL") reconstruction.

12 Claims, 33 Drawing Sheets

(52) U.S. Cl.
CPC .............. *A61B 2017/0409* (2013.01); *A61B 2017/0432* (2013.01); *A61F 2002/0835* (2013.01); *A61F 2002/0852* (2013.01); *A61F 2002/0858* (2013.01); *A61F 2002/0882* (2013.01)

(56) References Cited

U.S. PATENT DOCUMENTS

| | | |
|---|---|---|
| 4,851,005 A | 7/1989 | Hunt et al. |
| 4,870,957 A | 10/1989 | Goble et al. |
| 4,960,420 A | 10/1990 | Goble et al. |
| 4,988,351 A | 1/1991 | Paulos et al. |
| 5,037,422 A | 8/1991 | Hayhurst et al. |
| 5,161,916 A | 11/1992 | White et al. |
| 5,167,665 A | 12/1992 | McKinney |
| 5,176,682 A | 1/1993 | Chow |
| 5,192,303 A | 3/1993 | Gatturna et al. |
| 5,197,983 A | 3/1993 | Berman et al. |
| 5,209,756 A | 5/1993 | Seedhom et al. |
| 5,222,963 A | 6/1993 | Brinkerhoff et al. |
| 5,224,946 A | 7/1993 | Hayhurst et al. |
| 5,246,443 A | 9/1993 | Mai |
| 5,268,001 A | 12/1993 | Nicholson et al. |
| 5,326,205 A | 7/1994 | Anspach, Jr. et al. |
| 5,336,240 A | 8/1994 | Metzler et al. |
| 5,354,298 A | 10/1994 | Lee et al. |
| 5,372,599 A | 12/1994 | Martins |
| 5,380,334 A | 1/1995 | Torrie et al. |
| 5,397,356 A | 3/1995 | Goble et al. |
| 5,417,691 A | 5/1995 | Hayhurst |
| 5,417,712 A | 5/1995 | Whittaker et al. |
| 5,472,452 A | 12/1995 | Trott |
| 5,480,403 A | 1/1996 | Lee et al. |
| 5,486,197 A | 1/1996 | Le et al. |
| 5,500,001 A | 3/1996 | Trott |
| 5,501,683 A | 3/1996 | Trott |
| 5,501,695 A | 3/1996 | Anspach, Jr. et al. |
| 5,505,735 A | 4/1996 | Li |
| 5,522,844 A | 6/1996 | Johnson |
| 5,522,845 A | 6/1996 | Wenstrom, Jr. |
| 5,522,846 A | 6/1996 | Bonutti |
| 5,545,180 A | 8/1996 | Le et al. |
| 5,554,171 A | 9/1996 | Gatturna et al. |
| 5,569,306 A | 10/1996 | Thal |
| 5,601,557 A | 2/1997 | Hayhurst |
| 5,618,314 A | 4/1997 | Harwin et al. |
| 5,628,751 A | 5/1997 | Sander et al. |
| 5,632,748 A | 5/1997 | Beck, Jr. et al. |
| 5,643,274 A | 7/1997 | Sander et al. |
| 5,643,321 A | 7/1997 | McDevitt |
| 5,645,589 A | 7/1997 | Li |
| 5,649,963 A | 7/1997 | McDevitt |
| 5,702,215 A | 12/1997 | Li |
| 5,707,395 A | 1/1998 | Li |
| 5,713,903 A | 2/1998 | Sander et al. |
| 5,718,717 A | 2/1998 | Bonutti |
| 5,720,753 A | 2/1998 | Sander et al. |
| 5,725,557 A | 3/1998 | Gatturna et al. |
| 5,733,306 A | 3/1998 | Bonutti |
| 5,741,282 A | 4/1998 | Anspach, III et al. |
| 5,749,899 A | 5/1998 | Bardin |
| 5,782,865 A | 7/1998 | Grotz |
| 5,797,963 A | 9/1998 | McDevitt |
| 5,814,071 A | 9/1998 | McDevitt et al. |
| 5,814,072 A | 9/1998 | Bonutti |
| 5,849,004 A | 12/1998 | Bramlet |
| 5,891,168 A | 4/1999 | Thal |
| RE36,289 E | 8/1999 | Le et al. |
| 5,948,000 A | 9/1999 | Larsen et al. |
| 5,948,002 A | 9/1999 | Bonutti |
| 5,957,953 A | 9/1999 | DiPoto et al. |
| 5,964,764 A | 10/1999 | West, Jr. et al. |
| 5,968,078 A | 10/1999 | Grotz |
| 5,980,558 A | 11/1999 | Wiley |
| 6,007,566 A | 12/1999 | Wenstrom, Jr. |
| 6,022,373 A | 2/2000 | Li |
| 6,024,758 A | 2/2000 | Thal |
| 6,063,037 A | 5/2000 | Mittermeier et al. |
| 6,077,292 A | 6/2000 | Bonutti |
| 6,086,591 A | 7/2000 | Bojarski |
| 6,146,406 A | 11/2000 | Shluzas et al. |
| 6,149,669 A | 11/2000 | Li |
| 6,203,565 B1 | 3/2001 | Bonutti et al. |
| 6,241,732 B1 | 6/2001 | Overaker et al. |
| 6,287,324 B1 | 9/2001 | Yarnitsky et al. |
| 6,312,448 B1 | 11/2001 | Bonutti |
| 6,319,269 B1 | 11/2001 | Li |
| 6,328,758 B1 | 12/2001 | Tornier et al. |
| 6,464,713 B2 | 10/2002 | Bonutti |
| RE37,963 E | 1/2003 | Thal |
| 6,540,770 B1 | 4/2003 | Tornier et al. |
| 6,544,281 B2 | 4/2003 | Elattrache et al. |
| 6,547,800 B2 | 4/2003 | Foerster et al. |
| 6,554,862 B2 | 4/2003 | Hays et al. |
| 6,562,071 B2 | 5/2003 | Jaervinen |
| 6,582,453 B1 | 6/2003 | Tran et al. |
| 6,585,730 B1 | 7/2003 | Foerster |
| 6,616,694 B1 | 9/2003 | Hart |
| 6,632,224 B2 | 10/2003 | Cachia et al. |
| 6,635,073 B2 | 10/2003 | Bonutti |
| 6,641,597 B2 | 11/2003 | Burkhart et al. |
| 6,648,890 B2 | 11/2003 | Culbert et al. |
| 6,652,561 B1 | 11/2003 | Tran |
| 6,656,183 B2 | 12/2003 | Colleran et al. |
| 6,660,022 B1 | 12/2003 | Li et al. |
| 6,660,023 B2 | 12/2003 | McDevitt et al. |
| 6,673,094 B1 | 1/2004 | McDevitt et al. |
| 6,689,135 B2 | 2/2004 | Enayati |
| 6,692,516 B2 | 2/2004 | West, Jr. et al. |
| 6,770,076 B2 | 8/2004 | Foerster |
| 6,840,953 B2 | 1/2005 | Martinek |
| 6,846,313 B1 | 1/2005 | Rogers et al. |
| 6,887,271 B2 | 5/2005 | Justin et al. |
| 6,932,834 B2 | 8/2005 | Lizardi et al. |
| 7,008,451 B2 | 3/2006 | Justin et al. |
| 7,037,324 B2 | 5/2006 | Martinek |
| 7,087,073 B2 | 8/2006 | Bonutti |
| 7,144,413 B2 | 12/2006 | Wilford et al. |
| 7,144,415 B2 | 12/2006 | Del Rio et al. |
| 7,201,754 B2 | 4/2007 | Stewart et al. |
| 7,226,469 B2 | 6/2007 | Benavitz et al. |
| 7,235,100 B2 | 6/2007 | Martinek |
| 7,309,346 B2 | 12/2007 | Martinek |
| 7,309,355 B2 | 12/2007 | Donnelly et al. |
| 7,329,272 B2 | 2/2008 | Burkhart et al. |
| 7,329,281 B2 | 2/2008 | Hays et al. |
| 7,381,213 B2 | 6/2008 | Lizardi |
| 7,520,898 B2 | 4/2009 | Re et al. |
| 7,556,640 B2 | 7/2009 | Foerster |
| 7,572,283 B1 | 8/2009 | Meridew |
| 7,588,586 B2 | 9/2009 | Whittaker |
| 7,611,521 B2 | 11/2009 | Lubbers et al. |
| D605,763 S | 12/2009 | Griffis, III et al. |
| 7,651,528 B2 | 1/2010 | Montgomery et al. |
| 7,674,274 B2 | 3/2010 | Foerster et al. |
| 7,699,893 B2 | 4/2010 | Donnelly et al. |
| 7,713,285 B1 | 5/2010 | Stone et al. |
| 7,828,802 B2 * | 11/2010 | Levy .............. A61B 17/68 606/300 |
| 7,833,254 B2 | 11/2010 | Celli et al. |
| 7,846,162 B2 | 12/2010 | Nelson et al. |
| 7,862,612 B2 | 1/2011 | Re et al. |
| 7,879,094 B2 | 2/2011 | Baird et al. |
| 7,896,901 B2 | 3/2011 | Whittaker |
| 7,901,456 B2 | 3/2011 | Justin et al. |
| 7,918,879 B2 | 4/2011 | Yeung et al. |
| 7,967,861 B2 | 6/2011 | Montgomery et al. |
| 8,048,158 B2 | 11/2011 | Hays et al. |
| 8,062,334 B2 | 11/2011 | Green et al. |
| 8,069,858 B2 | 12/2011 | Gall |
| 8,080,044 B2 | 12/2011 | Biedermann et al. |
| 8,128,663 B2 | 3/2012 | Zucherman et al. |
| 8,162,942 B2 | 4/2012 | Coati et al. |
| 8,192,490 B2 | 6/2012 | Baird et al. |

(56) References Cited

U.S. PATENT DOCUMENTS

| | | | |
|---|---|---|---|
| 8,221,479 B2 | 7/2012 | Glazer et al. | |
| 8,317,863 B2 | 11/2012 | Cauldwell et al. | |
| 8,414,647 B2 | 4/2013 | Baird et al. | |
| 8,430,933 B2 | 4/2013 | Gall | |
| 8,435,294 B2 | 5/2013 | Montgomery et al. | |
| 8,523,902 B2 | 9/2013 | Heaven et al. | |
| 8,652,208 B2 | 2/2014 | Baird et al. | |
| 8,747,469 B2 | 6/2014 | Wang et al. | |
| 8,906,060 B2 | 12/2014 | Hart | |
| 8,986,345 B2 | 3/2015 | Denham et al. | |
| 9,044,313 B2 | 6/2015 | Heaven | |
| 9,155,574 B2 | 10/2015 | Saravia et al. | |
| 9,510,816 B2 | 12/2016 | McDevitt et al. | |
| 2003/0065390 A1* | 4/2003 | Justin | A61F 2/0811 623/13.14 |
| 2003/0100903 A1 | 5/2003 | Cooper | |
| 2003/0195564 A1 | 10/2003 | Tran et al. | |
| 2004/0010287 A1 | 1/2004 | Bonutti | |
| 2004/0098053 A1 | 5/2004 | Tran | |
| 2004/0138683 A1 | 7/2004 | Shelton et al. | |
| 2004/0193217 A1 | 9/2004 | Lubbers et al. | |
| 2004/0230194 A1 | 11/2004 | Urbanski et al. | |
| 2006/0229617 A1 | 10/2006 | Meller et al. | |
| 2006/0282081 A1 | 12/2006 | Fanton et al. | |
| 2007/0027477 A1 | 2/2007 | Chudik | |
| 2008/0195221 A1 | 8/2008 | Howald et al. | |
| 2008/0221624 A1 | 9/2008 | Gooch | |
| 2009/0030516 A1 | 1/2009 | Imbert | |
| 2009/0043342 A1 | 2/2009 | Freedland | |
| 2009/0149884 A1 | 6/2009 | Snyder et al. | |
| 2009/0187216 A1 | 7/2009 | Schmieding et al. | |
| 2009/0248068 A1 | 10/2009 | Lombardo et al. | |
| 2010/0292732 A1 | 11/2010 | Hirotsuka et al. | |
| 2010/0033188 A1 | 12/2010 | Hart | |
| 2011/0112550 A1 | 5/2011 | Heaven et al. | |
| 2013/0338710 A1 | 12/2013 | Heaven et al. | |
| 2014/0046369 A1 | 2/2014 | Heaven et al. | |

FOREIGN PATENT DOCUMENTS

| | | | |
|---|---|---|---|
| EP | 0409364 | 3/1991 | |
| EP | 0504915 | 9/1992 | |
| EP | 0574707 | 12/1993 | |
| EP | 0673624 | 11/1995 | |
| EP | 1348380 | 10/2003 | |
| EP | 2266469 | 12/2010 | |
| EP | 2488118 | 8/2012 | |
| FR | 2671717 | 7/1992 | |
| WO | 9515726 | 6/1995 | |
| WO | 1997/007741 | 3/1997 | |
| WO | 2002/032345 | 4/2002 | |
| WO | 2003/105700 | 12/2003 | |
| WO | 2006/055823 | 5/2006 | |
| WO | 2008/073588 | 6/2008 | |
| WO | WO 2008145984 A1 * | 12/2008 | A61F 2/0811 |
| WO | 2009/154791 | 12/2009 | |
| WO | 2010/088561 | 8/2010 | |
| WO | 2011/046982 | 4/2011 | |
| WO | 2012/093961 | 7/2012 | |
| WO | 2012/148693 | 11/2012 | |
| WO | 2015/059582 | 4/2015 | |

OTHER PUBLICATIONS

Sherman et al., "The long-term followup of primary anterior cruciate ligament repair," The American Journal of Sports Medicine, vol. 19, No. 3, 243-255 (1991).

Whipple et al., "A Technique for Arthroscopic Anterior Cruciate Ligament Repair," Clinics in Sports Medicine, vol. 10, No. 3, 463-468 (1991).

Hecker et al., "Pull-out strength of suture anchors for rotator cuff and Bankart lesion repairs," The American Journal of Sports Medicine, vol. 21, No. 6, 874-879 (1993).

Green et al., "Arthroscopic Versus Open Bankart Procedures: A Comparison of Early Morbidity and Complications," The Journal of Arthroscopic and Related Surgery, vol. 9, No. 4, 371-374 (1993).

Shall et al., "Soft Tissue Reconstruction in the Shoulder," The American Journal of Sports Medicine, vol. 22, No. 5, 715-718 (1994).

Richards et al., "A Biomechanical Analysis of Two Biceps Tenodesis Fixation Techniques," Arthroscopy: The Journal of Arthroscopic and Related Surgery, vol. 21, No. 7, 2005: pp. 861-866.

"Executive Interview: Chris Fair, Chief Operations Officer; Ken Gall, Ph.D., Director & Chief Techical Officer, MedShape Solutions, Inc.," Orthopreneur, pp. 22-25, Jan./Feb. 2010.

Yakacki et al., "The Design and Pullout Strength of a Novel Shape-Memory PEEK Suture Anchor," 56th Annual Meeting of the Orthopaedic Research Society, Poster No. 1801 presented on approximately Mar. 1, 2010.

"Scope This Out: A Technical Pearls Newsletter for Arthroscopists," Spring 2010, pp. 1-8, vol. 12, No. 1, Arthrex, Inc.

International Search Report and Written Opinion dated Aug. 19, 2010 for International Application No. PCT/US2010/022661, filed Jan. 29, 2010.

International Search Report and Written Opinion dated Dec. 9, 2010, for International Patent Application No. PCT/US2010/052398, filed Oct. 12, 2010.

USS Sports Medicine presents POLYSORB 3mm Soft Tissue Anchor System, US Surgical Corp., Date of Publication unknown; 2 pages.

International Search Report and Written Opinion dated Jan. 18, 2013 for International Application No. PCT/US2012/058786, filed Oct. 4, 2012.

International Preliminary Report on Patentability dated Apr. 7, 2015 for International Application No. PCT/US2013/063275, filed Oct. 3, 2013.

Boileau et al., "Arthroscopic Biceps Tenodesis: A New Technique Using Bioabsorbable Interference Screw Fixation," J Arthrosc Related Surgery, vol. 18, No. 9, (Nov.-Dec. 2002), 1002-1012.

International Preliminary Report on Patentability dated Aug. 2, 2011 for International Application No. PCT/US2010/022661, filed Jan. 29, 2010.

International Search Report and written Opinion dated Aug. 6, 2012, for International Patent Application No. PCT/US2012/033392, filed Apr. 12, 2012.

International Search Report and Written Opinion dated Feb. 3, 2014 for International Application No. PCT/US2013/063275, filed Oct. 3, 2013.

Extended European Search Report dated Oct. 13, 2016, PCT/US2014/021774; 7 pages.

* cited by examiner

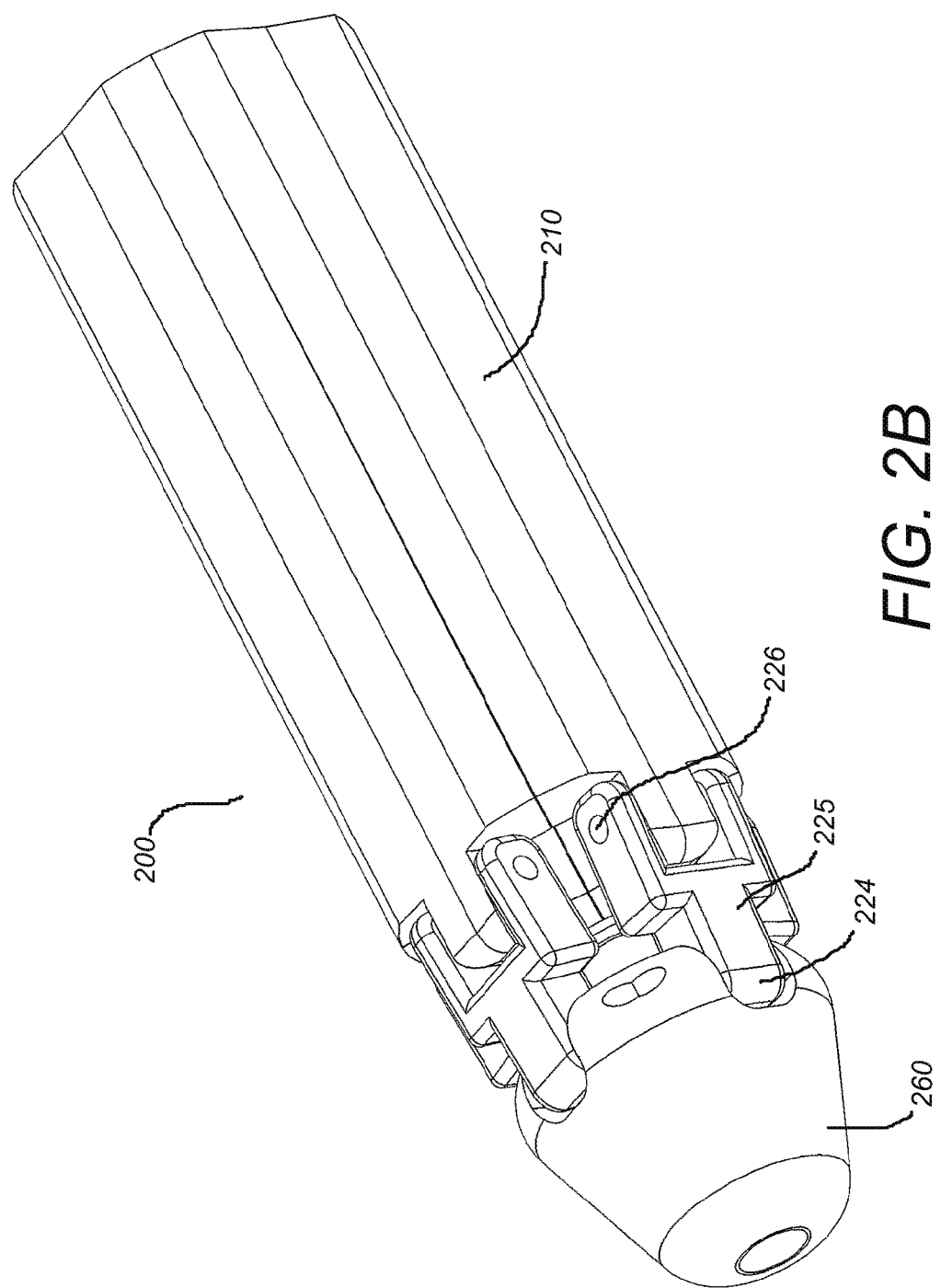

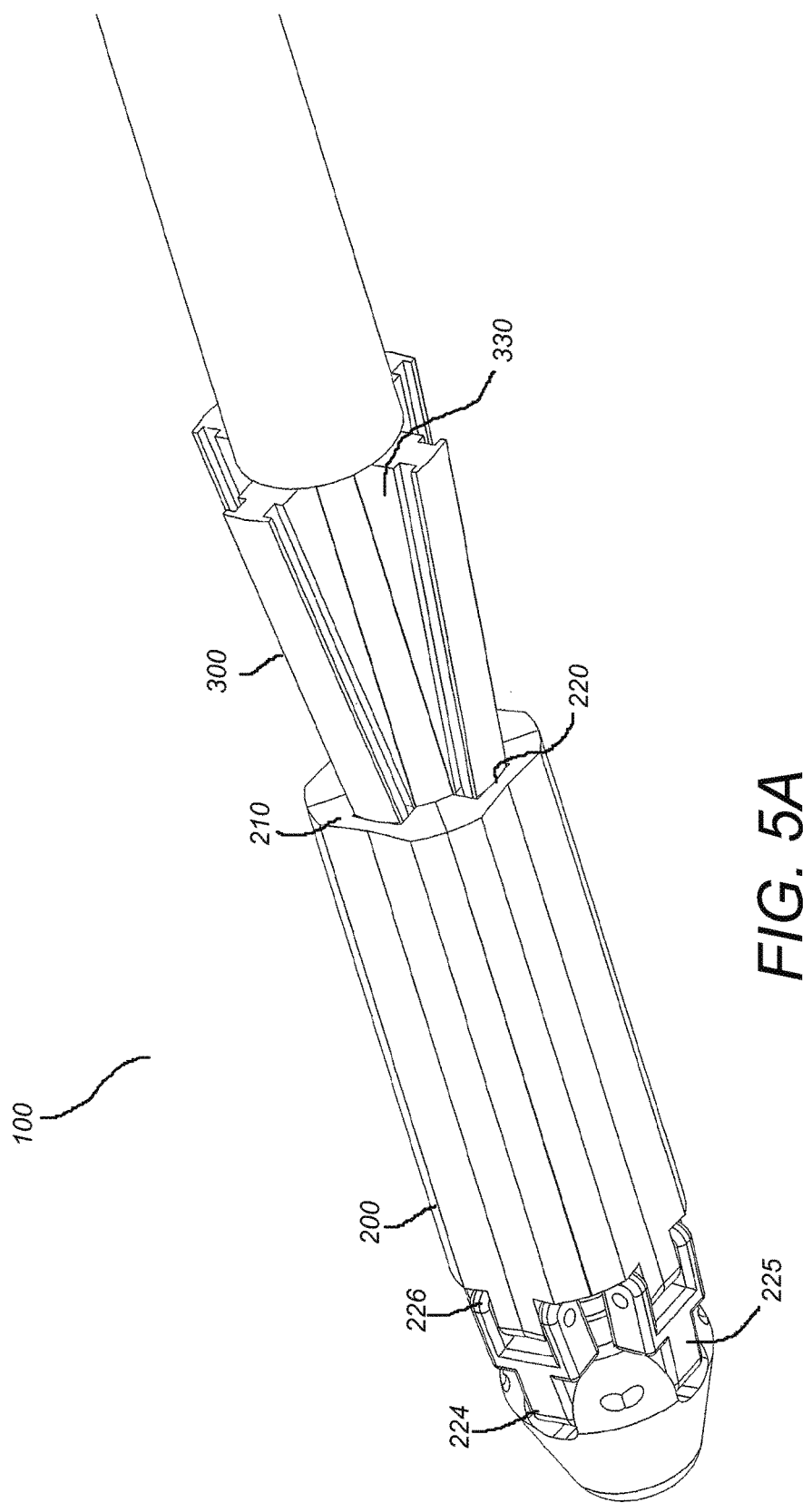

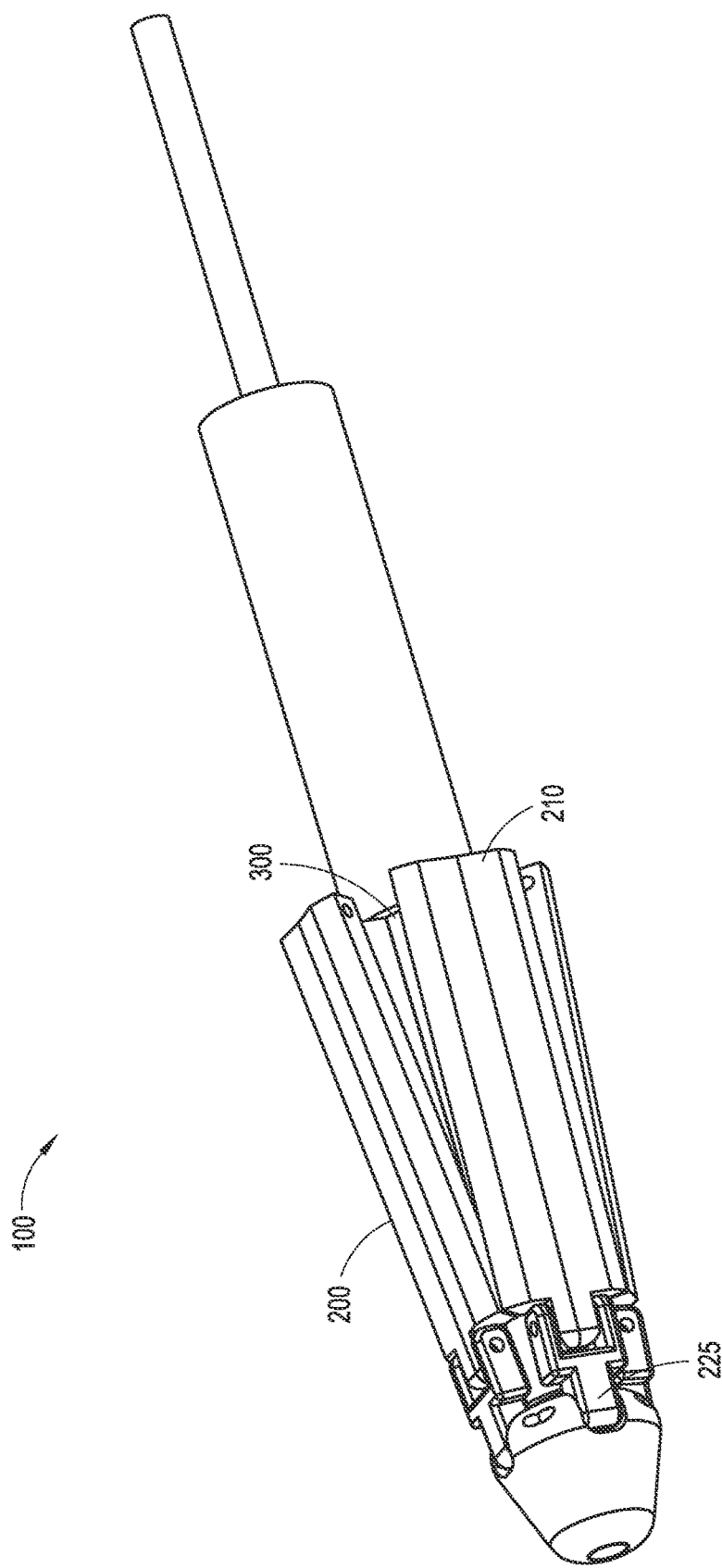

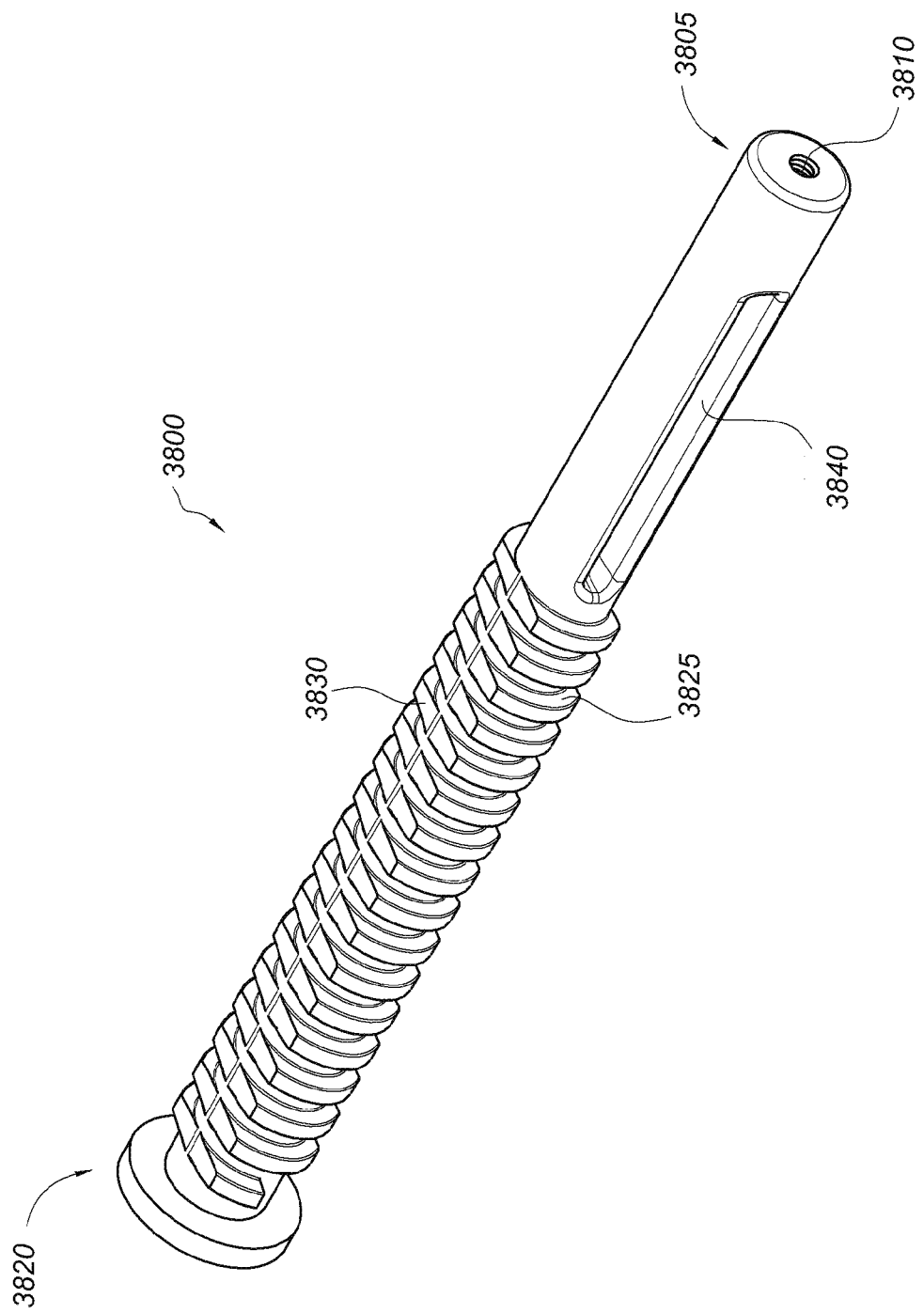

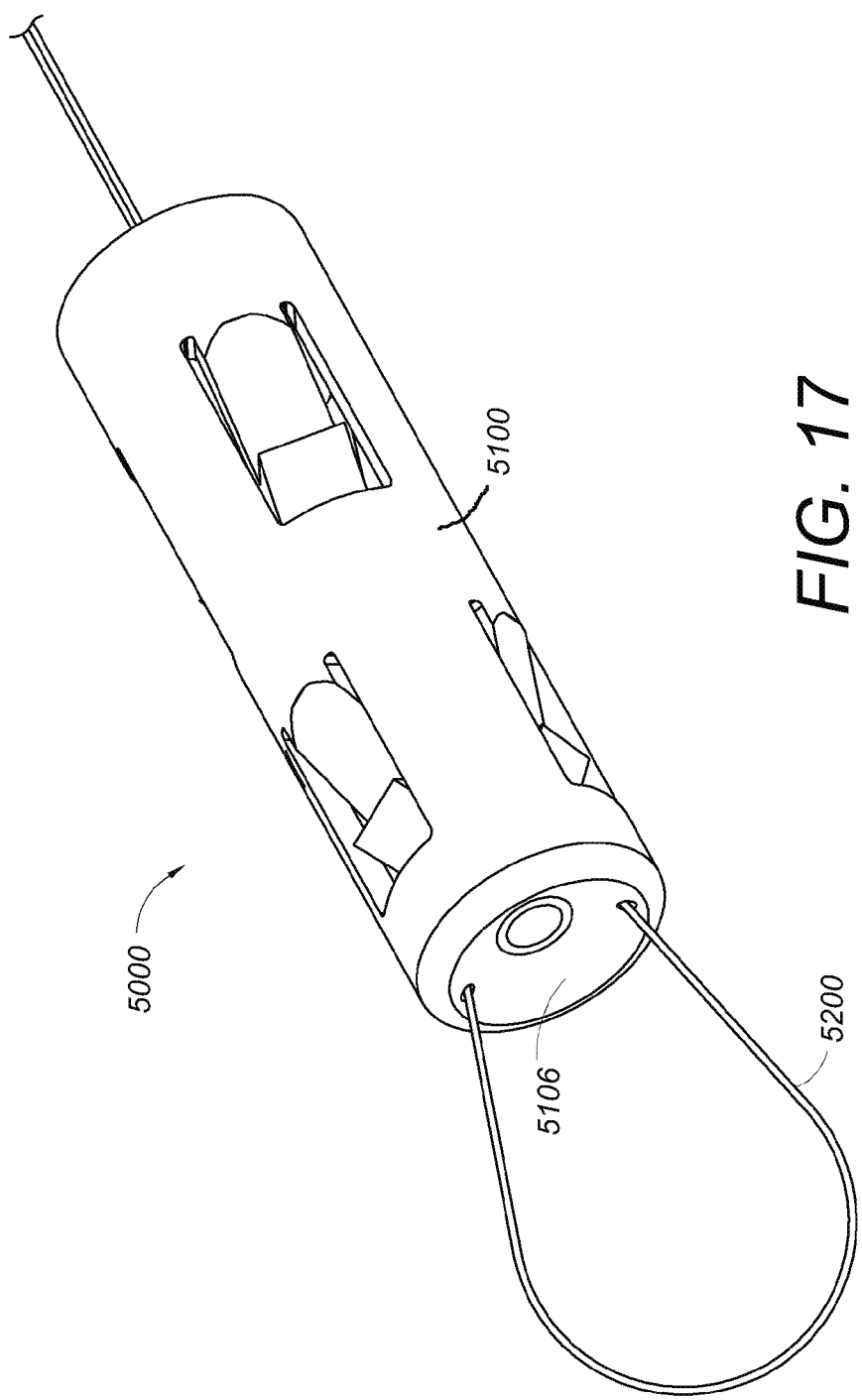

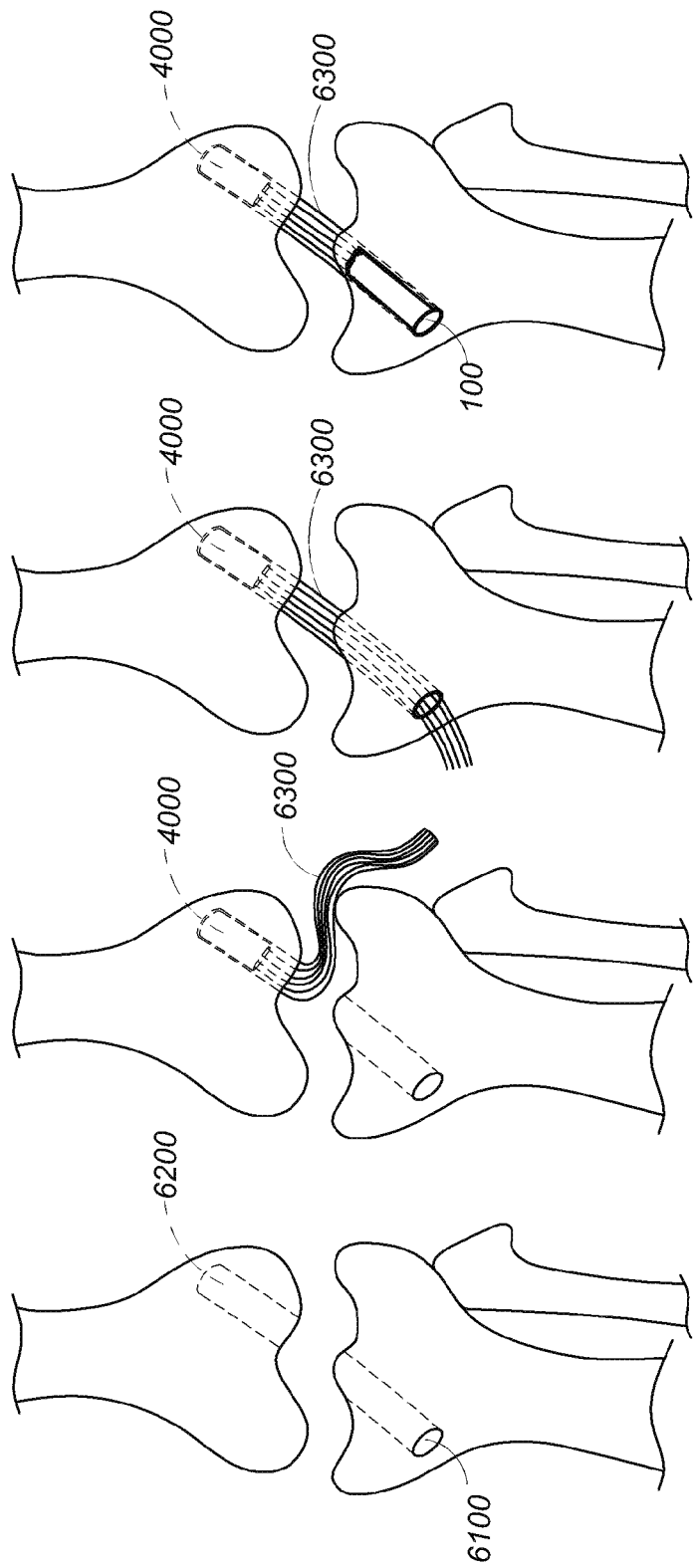

SYSTEM AND METHOD FOR SECURING TISSUE TO BONE

INCORPORATION BY REFERENCE TO ANY PRIORITY APPLICATION

This application claims the benefit and priority of U.S. Provisional Application Ser. No. 61/801,255, filed Mar. 15, 2013, which is hereby incorporated by reference in its entirety.

BACKGROUND OF THE INVENTION

Field of the Invention

The present invention relates to medical devices and procedures. More particularly, the present invention relates to devices and methods for securing soft tissue to a rigid material such as bone. Systems and methods are disclosed herein of fixing tissue such as tendon or ligament to bone in orthopedic procedures.

Description of the Related Art

There are several medical procedures where a surgeon needs to attach soft connective tissue such as tendons or ligaments to bone. One common example is an anterior cruciate ligament ("ACL") reconstruction, a surgical procedure usually performed for the treatment of a torn ACL. The ACL is one of four major ligaments of the knee. An ACL reconstruction may be performed as an isolated procedure, but is often performed alongside the treatment of meniscus tears and cartilage injuries as part of a multiple-repair surgery.

An ACL reconstruction is a procedure that replaces the injured ACL with a tissue graft generally formed from the patient's patellar tendon or hamstring tendon or the ligament of a cadaver. To perform an ACL reconstruction, a surgical procedure is used, typically requiring the multiple steps of: harvesting and sizing the tissue graft, securing the tissue graft to the end of a pin, removing the existing damaged ACL, drilling a tunnel that creates a bore through the tibial bone and a blind hole in the femoral bone, passing the pin and tissue graft through the bore and into the blind hole, and screwing a first anchor into the blind hole of the femur and a second anchor into the bore of the tibia to capture the tissue graft against the bone and solidly affix the tissue to the bone. Even as an isolated procedure, ACL reconstruction is difficult to perform arthroscopically. Systems recently brought to market still require multiple steps and tools.

SUMMARY OF THE INVENTION

Disclosed herein are various embodiments of bone anchors and methods for performing anterior cruciate ligament (ACL) repair that may address the aforementioned needs. In some embodiments of the present invention, there is provided a method of anterior cruciate ligament (ACL) repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor comprises an expandable anchor body having an internal cavity and a spreader, and sliding the expander into the internal cavity, thereby causing at least a portion of the anchor body to expand outward, wherein upon completion of the expansion, at least a portion of the anchor body adjacent to the distal opening of the bone tunnel is expanded.

In some embodiments of the present invention, upon insertion of the anchor, the anchor extends substantially the entire length of the bone tunnel. In some embodiments upon expansion of the anchor, at least a portion of the anchor is not expanded outward. In further embodiments, the portion not expanded outward comprises an anchor tip.

In some embodiments of the present invention, there is provided a method of ACL repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor is greater than about 30 mm long and comprises an expandable anchor body having an internal cavity and a spreader, and sliding the expander into the internal cavity, thereby causing at least a portion of the anchor body to expand outward, wherein upon completion of the expansion, at least a portion of the anchor body adjacent to the distal opening of the bone tunnel is expanded.

In some embodiments of the present invention, there is provided a method of ACL repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor is greater than about 35 mm long and comprises an expandable anchor body having an internal cavity and a spreader, and sliding the expander into the internal cavity, thereby causing at least a portion of the anchor body to expand outward, wherein upon completion of the expansion, at least a portion of the anchor body adjacent to the distal opening of the bone tunnel is expanded.

In some embodiments of the present invention, there is provided a method of ACL repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor is greater than about 40 mm long and comprises an expandable anchor body having an internal cavity and a spreader, and sliding the expander into the internal cavity, thereby causing at least a portion of the anchor body to expand outward, wherein upon completion of the expansion, at least a portion of the anchor body adjacent to the distal opening of the bone tunnel is expanded.

In other embodiments of the present invention, there is provided a method of anterior cruciate ligament (ACL) repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor comprises an expandable anchor body having an internal cavity and a spreader, and inserting the expander into the internal cavity, thereby causing at least a portion of the anchor body to expand outward, wherein upon completion of the expansion, the expanded portion of the anchor body is expanded substantially uniformly along its length.

In some embodiments of the present invention upon insertion of the anchor, the anchor extends substantially the entire length of the bone tunnel. In some embodiments upon expansion of the anchor, at least a portion of the anchor is not expanded outward. In further embodiments the portion not expanded outward comprises an anchor tip.

In some embodiments of the present invention, there is provided a method of ACL repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor is greater than about 30 mm long and comprises an expandable anchor body having an internal cavity and a spreader, and inserting the expander into the internal cavity, thereby causing at least a portion of the anchor body to expand outward, wherein upon completion of the expansion, the expanded portion of the anchor body is expanded substantially uniformly along its length.

In some embodiments of the present invention, there is provided a method of ACL repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor is greater than about 35 mm long and comprises an expandable anchor body having an internal cavity and a spreader, and inserting the expander into the internal cavity, thereby causing at least a portion of the anchor body to expand outward, wherein upon completion of the expansion, the expanded portion of the anchor body is expanded substantially uniformly along its length.

In some embodiments of the present invention, there is provided a method of ACL repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, inserting an anchor into a proximal opening of the bone tunnel to a position where a distal end of the anchor is adjacent to a distal opening of the bone tunnel, wherein the anchor is greater than about 40 mm long and comprises an expandable anchor body having an internal cavity and a spreader, and inserting the expander into the internal cavity, thereby causing at least a portion of the anchor body to expand outward, wherein upon completion of the expansion, the expanded portion of the anchor body is expanded substantially uniformly along its length.

In other embodiments of the present invention, there is provided a method of anterior cruciate ligament (ACL) repair, comprising forming a bone tunnel in a tibia, wherein the bone tunnel comprises a proximal opening on one side of the tibia and a distal opening on an opposite side of the tibia, passing soft tissue through the bone tunnel, securing the soft tissue to a femur, measuring the length of the bone tunnel, selecting an anchor from a plurality of possible anchors based on the measurement, inserting the anchor into a proximal opening of the bone tunnel to a position where a distal end of the anchor is adjacent to a distal opening of the bone tunnel, wherein the anchor comprises an expandable anchor body having an internal cavity and a spreader, and inserting the spreader into the internal cavity, thereby causing at least a portion of the anchor body to expand outward, wherein upon completion of the expansion, at least a portion of the anchor body adjacent to the distal opening of the bone tunnel is expanded. In some embodiments selecting the anchor comprises selecting a length of anchor among a plurality of possible lengths.

In other embodiments of the present invention, there is provided an expandable bone anchor, comprising an anchor body and a spreader. The anchor body comprises a distal tapered anchor tip and a plurality of rigid side portions extending proximally from the anchor tip, each side portion coupled to the anchor tip through a double hinge. The spreader is configured to advance distally into the anchor body, thereby causing the rigid side portions to expand outward.

In some embodiments the spreader is coupled to the side portions. In some embodiments the spreader is slidably coupled to the side portions. In further embodiments the spreader comprises a plurality of longitudinal tracks and each side portion is coupled to one of the tracks such that the side portions can slide longitudinally along the tracks.

In some embodiments of the present invention, there is provided an expandable bone anchor, comprising an anchor body and a spreader. The anchor body comprises a distal tapered anchor tip and a plurality of rigid side portions extending proximally from the anchor tip, each side portion coupled to the anchor tip through a double hinge. The spreader is configured to advance distally into the anchor body, thereby causing the rigid side portions to expand outward, wherein the spreader comprises at least a portion that is tapered distally.

In some embodiments of the present invention, there is provided an expandable bone anchor, comprising an anchor body and a spreader. The anchor body comprises a distal tapered anchor tip and a plurality of rigid side portions extending proximally from the anchor tip, each side portion coupled to the anchor tip through a double hinge. The spreader is configured to advance distally into the anchor body, thereby causing the rigid side portions to expand outward. In some embodiments the anchor tip comprises a proximal locking member and the spreader comprises a distal locking member, wherein the two locking members are configured to lock together upon maximal distal advancement of the spreader. In further embodiments, the proximal locking member on the tip comprises a post having an outwardly protruding ridge and the distal locking member on the spreader comprises a hollow cylinder configured to receive the post. In further embodiments the hollow cylinder comprises a groove on an inside surface configured to receive the protruding ridge. In further embodiments the hollow cylinder comprises expandable tabs.

In some embodiments of the present invention, there is provided an expandable bone anchor, comprising an anchor body and a spreader. The anchor body comprises a distal tapered anchor tip and a plurality of rigid side portions extending proximally from the anchor tip, each side portion coupled to the anchor tip through a double hinge. The spreader is configured to advance distally into the anchor body, thereby causing the rigid side portions to expand outward, wherein upon maximal expansion, the rigid side portions are expanded to a substantially uniform extent along their length.

In other embodiments of the present invention, there is provided an expandable bone anchor, comprising an anchor body and a spreader. The anchor body comprises a distal tapered anchor tip, a plurality of first expandable side portions, and a plurality of second expandable side portions. The plurality of first expandable side portions are positioned at a proximal end of the anchor body, wherein the first expandable side portions expand by bending outward such that the first expandable side portion extends outward to a greater extent at its proximal portion than at its distal portion. The plurality of second expandable side portions are positioned distally of the first expandable side portions, wherein the second expandable side portions expand by bending outward such that the second expandable side portion extends outward to a greater extent at its distal portion than at its proximal portion. The spreader is configured to advance distally into the anchor body, thereby causing the first and second expandable side portions to expand outward.

In some embodiments the first and second expandable side portions comprise bone-engaging features. In further embodiments the bone engage features comprise teeth. In some embodiments the bone engage features comprise ridges.

In some embodiments of the present invention, there is provided an expandable bone anchor, comprising an anchor body and a spreader. The anchor body comprises a distal tapered anchor tip, a plurality of first expandable side portions, and a plurality of second expandable side portions. The plurality of first expandable side portions are positioned at a proximal end of the anchor body, wherein the first expandable side portions expand by bending outward such that the first expandable side portion extends outward to a greater extent at its proximal portion than at its distal portion. The plurality of second expandable side portions are positioned distally of the first expandable side portions, wherein the second expandable side portions expand by bending outward such that the second expandable side portion extends outward to a greater extent at its distal portion than at its proximal portion. The spreader is configured to advance distally into the anchor body, thereby causing the first and second expandable side portions to expand outward, wherein the first and second expandable side portion is formed by cuts in a side wall of the anchor body. In some embodiments the anchor body tapers distally upon substantially its whole length. In some embodiments the anchor tip has a hemispherical shape. In some embodiments the anchor tip has a conical shape. In some embodiments the second expandable side portions comprise a protrusion extending into a central cavity within the anchor body, wherein advancement of the spreader into the central cavity causes the spreader to contact the protrusion, thereby causing the second expandable side portions to expand outward.

In some embodiments of the present invention, there is provided an expandable bone anchor, comprising an anchor body and a spreader. The anchor body comprises a distal tapered anchor tip, a plurality of first expandable side portions, and a plurality of second expandable side portions. The plurality of first expandable side portions are positioned at a proximal end of the anchor body, wherein the first expandable side portions expand by bending outward such that the first expandable side portion extends outward to a greater extent at its proximal portion than at its distal portion. The plurality of second expandable side portions are positioned distally of the first expandable side portions, wherein the second expandable side portions expand by bending outward such that the second expandable side portion extends outward to a greater extent at its distal portion than at its proximal portion. The spreader is configured to advance distally into the anchor body, thereby causing the first and second expandable side portions to expand outward, wherein the spreader comprises at least a portion that is tapered distally.

In some embodiments of the present invention, there is provided an expandable bone anchor, comprising an anchor body and a spreader. The anchor body comprises a distal tapered anchor tip, a plurality of first expandable side portions, and a plurality of second expandable side portions. The plurality of first expandable side portions are positioned at a proximal end of the anchor body, wherein the first expandable side portions expand by bending outward such that the first expandable side portion extends outward to a greater extent at its proximal portion than at its distal portion. The plurality of second expandable side portions are positioned distally of the first expandable side portions, wherein the second expandable side portions expand by bending outward such that the second expandable side portion extends outward to a greater extent at its distal portion than at its proximal portion. The spreader is configured to advance distally into the anchor body, thereby causing the first and second expandable side portions to expand outward, wherein the spreader has a substantially constant diameter along its length. In some embodiments the spreader comprises a circumferential ridge positioned at or adjacent to its proximal end.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting.

FIG. 2B depicts a perspective proximal view of one embodiment of an anchor body in an unexpanded state.

FIG. 5A depicts a perspective view of one embodiment of a tissue anchoring device in an unexpanded/undeployed state.

FIG. 5B depicts a perspective proximal view of one embodiment of a tissue anchoring device in an expanded/deployed state.

FIG. 15F shows a perspective view of one embodiment of an actuator shaft component of an insertion tool.

FIG. 17 shows a perspective view of one embodiment of a tissue anchoring device comprising a tissue capture suture loop.

FIGS. 18A-18D depict four frontal views of the bones surrounding the human knee and one embodiment of a method of securing soft tissue to the bones using a tissue anchoring device.

DETAILED DESCRIPTION OF THE CERTAIN EMBODIMENTS

Figure 1:
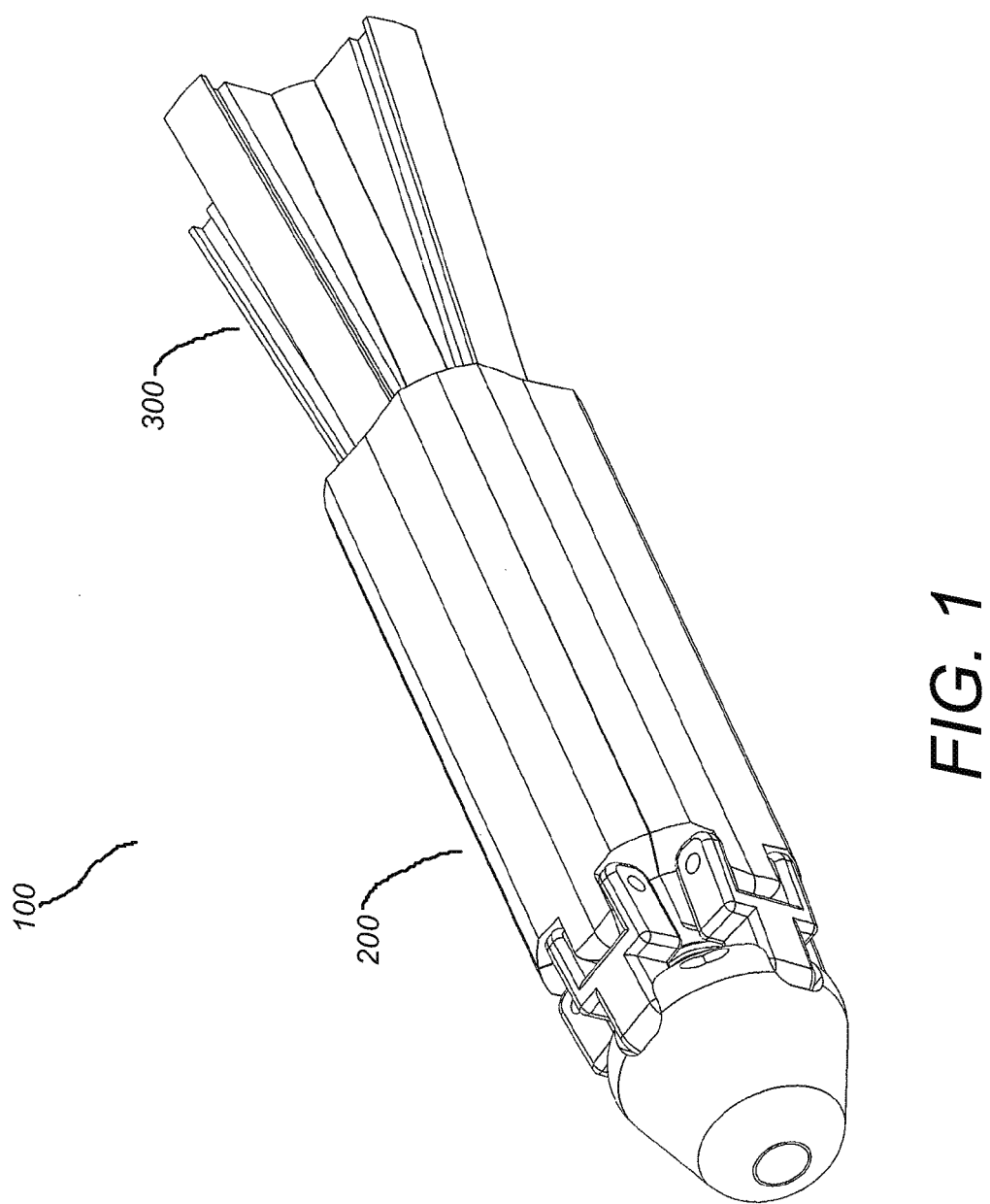
FIG. 1 depicts a perspective proximal view of one embodiment of a tissue anchoring device in an unexpanded/undeployed state.

In the following detailed description, reference is made to the accompanying drawings, which form a part of the present disclosure. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, and designed in a wide variety of different configurations, all of which are explicitly contemplated and form part of this disclosure.

The terminology used herein is for the purpose of describing particular embodiments only and is not intended to be limiting of the disclosure. It will be understood by those within the art that if a specific number of a claim element is intended, such intent will be explicitly recited in the claim, and in the absence of such recitation, no such intent is present. For example, as used herein, the singular forms "a", "an" and "the" are intended to include the plural forms as well, unless the context clearly indicates otherwise. As used herein, the term "and/or" includes any and all combinations of one or more of the associated listed items. It will be further understood that the terms "comprises," "comprising," "have," "having," "includes," and "including," when used in this specification, specify the presence of stated features, integers, steps, operations, elements, and/or components, but do not preclude the presence or addition of one or more other features, integers, steps, operations, elements, components, and/or groups thereof. Expressions such as "at least one of," when preceding a list of elements, modify the entire list of elements and do not modify the individual elements of the list.

To assist in the description of the devices and methods described herein, some relational and directional terms are used. As recited within this disclosure, the "longitudinal axis" of a bone or component is the elongated axis running through the length of the bone or component.

"Connected" and "coupled," and variations thereof, as used herein include direct connections, such as being contiguously formed with, or glued, or otherwise attached directly to, on, within, etc. another element, as well as indirect connections where one or more elements are disposed between the connected elements. "Connected" and "coupled" may refer to a permanent or non-permanent (i.e., removable) connection.

"Secured" and variations thereof as used herein include methods by which an element is directly secured to another element, such as being glued, screwed, or otherwise fastened directly to, on, within, etc. another element, as well as indirect means of securing two elements together where one or more elements are disposed between the secured elements.

"Proximal" and "distal" are relational terms used herein to describe position from the perspective of a medical professional positioning a tissue anchoring device. For example, as compared to "distal," the term "proximal" refers to a position that is located more closely to the medical professional once inserted or implanted during surgery. Often, the proximal end of the fixation device includes, for example, the end that abuts an insertion tool. The distal end opposes the proximal end and often includes, for example, the end configured to be pushed furthest into a bone tunnel in a patient.

Embodiments disclosed herein relate to tissue anchoring devices and methods of anchoring soft tissue, such as for example, tendons or ligaments, to bone. The tissue anchoring devices of the present disclosure are each configured with multiple fixation sites along the length of the device.

Some embodiments disclosed herein relate generally to anchors for use in anchoring tissue or objects in a body. More specifically, some embodiments disclosed herein relate generally to anchors for use in anchoring soft tissue to bone in a body. Also some elements relate to individual components and subcomponents of the systems described herein, as well as methods of making and using the same. Some embodiments additionally relate to kits and components used in connection with the anchor. Although the following embodiments refer to the use of an anchor in anchoring tissue, a person of skill in the art will recognize that an anchor can be used to anchor any range of items within a body.

Various embodiments disclosed herein relate to anchors configured to attach soft tissue to bone, such as, for example, to attach an anterior cruciate ligament ("ACL") graft within a bone tunnel of a tibial bone. As described in more detail below with reference to individual embodiments, various anchors disclosed herein are configured to extend through substantially the length a bone tunnel. In some such embodiments, the anchors are configured to provide for expansion and fixation along the length of the anchor. In other embodiments disclosed herein, the anchors are configured to provide for expansion and fixation at various points along the length of the anchor.

FIG. 1A depicts a perspective view of one embodiment of a tissue anchoring device 100. The tissue anchoring device 100 of the current embodiment includes an anchor body 200 and a spreader 300. The spreader 300 is configured to slidably fit within a central bore of the anchor body 200.

FIG. 1B depicts a perspective view of one embodiment of a tissue anchoring device 100 in an expanded or deployed state. The tissue anchoring device 100 of the current embodiment includes an anchor body 200 and a spreader 300. The spreader 300 is configured to slidably fit within a central bore of the anchor body 200.

Figure 2A:
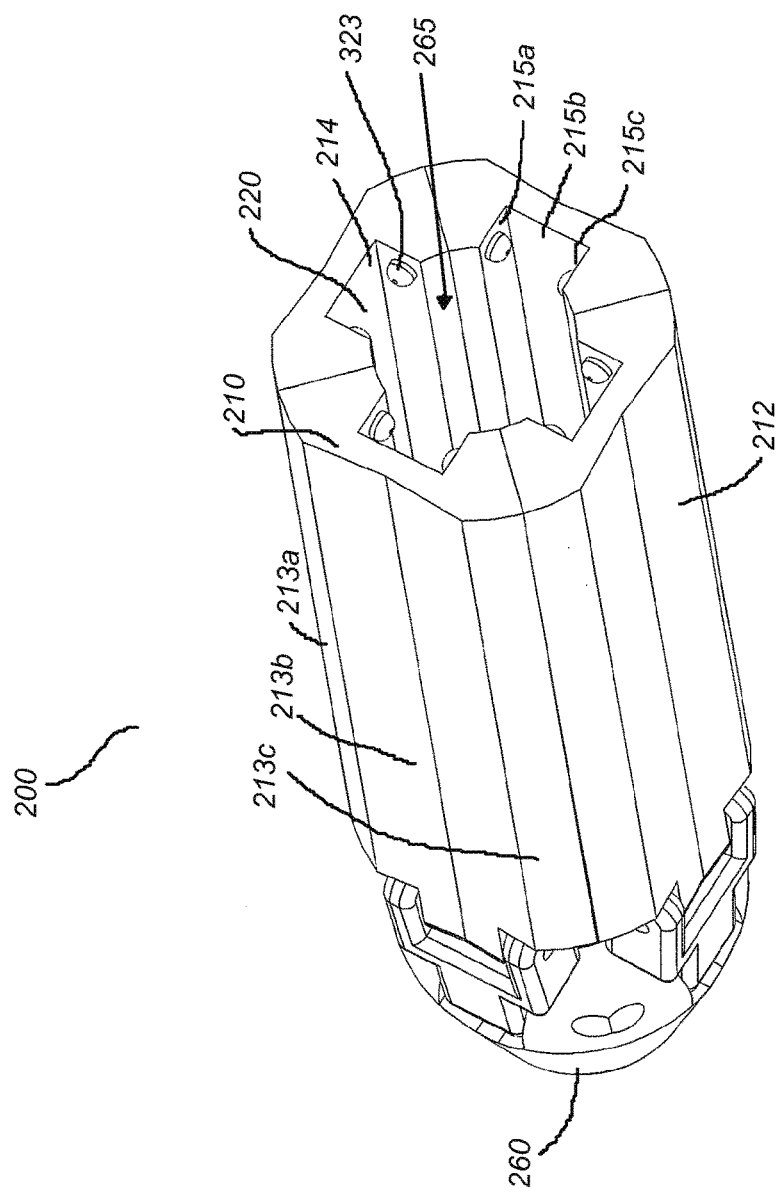
FIG. 2A depicts a perspective distal view of one embodiment of an anchor body in an unexpanded state.

The anchor body 200, shown in more detail in FIGS. 2A and 2B, includes four panels 210 (i.e., rigid side portions). In other embodiments, a different number of panels 210 may be present, such as, for example, three, five, six, seven, or eight panels 210. In various embodiments, when the panels 210 are in a first, unexpanded position, each panel 210 abuts a neighboring panel 210 on at least two sides. Each panel 210 has an outer surface 212 and an inner surface 214. In some embodiments, the outer surfaces 212 of the panels 210 together define the at least a portion of the shape of the anchor body 200. The outer surface 212 of each panel 210 includes one or more flat faces (e.g., faces 213a, 213b, and 213c). In such embodiments, when the panels 210 are in an unexpanded position, their outer surfaces 212 form a polyhedron. In other embodiments, the outer surface 212 of each panel 210 has a rounded face, and together the outer surfaces 212 of the panels 210 form a cylinder in an unexpanded position. In other embodiments, such as in FIG. 2A, the panels 210 have both rounded faces 213a, 213c and non-rounded faces 213b on the outer surface 212. In various embodiments, when the panels 210 are in an unexpanded position, the tissue anchoring device 100 is in a streamlined position such that there is little to no protrusion of the panels 210 radially outward. In some embodiments, the panels 210 are substantially rigid and do not flex during operation.

As shown in FIG. 2A, in various embodiments, the inner surfaces 214 of the panels 210 surround and define a central bore 265. Additionally, in some embodiments, the inner surface 214 of each panel 210 has a plurality of faces. For example, as shown in FIG. 2B, the inner surface 214 of some embodiments includes at least three faces (e.g., faces 215a, 215b, and 215c), which together define a groove 220. As described in more detail below, in various embodiments, the groove 220 is configured to receive a protrusion or track of the spreader 300.

In some embodiments, the panels 210 and the central bore 265 extend nearly the entire length of the anchor body 200. In some such embodiments, the anchor body 200 includes a distal tip 260 coupled to a distal end of the panels 210, which limits the panels 210 from actually extending the entire length of the anchor body 200. In various embodiments, the distal tip 260 is closed and rounded. As shown in FIG. 2B, each panel 210 is attached to the distal tip 260 via a hinge element 225. The distal tip 260 of some embodiments acts as a base of direct or indirect connection for the plurality of panels 210. In some embodiments, each hinge element 225 includes two pivoting connections (i.e., forming a double hinge)—a distal pivot 224 at a distal side of the hinge element 225, pivotally connecting the hinge element 225 to the distal tip 260, and a proximal pivot 226 at a proximal side of the hinge element 225, pivotally connecting the hinge element 225 to a panel 210.

In some embodiments, the panels 210 are configured to move from an unexpanded position to an expanded position via pivoting about the distal pivot 224 and the proximal pivot 226. In various embodiments, the panels 210 are urged to move from the unexpanded position to the expanded position upon insertion of a spreader 300 into the central bore 265 of the anchor body 200. The spreader 300, shown in more detail in FIGS. 3A-3C, is shaped and configured to facilitate displacement of the panels 210 of the anchor body 200.

Figure 3A:
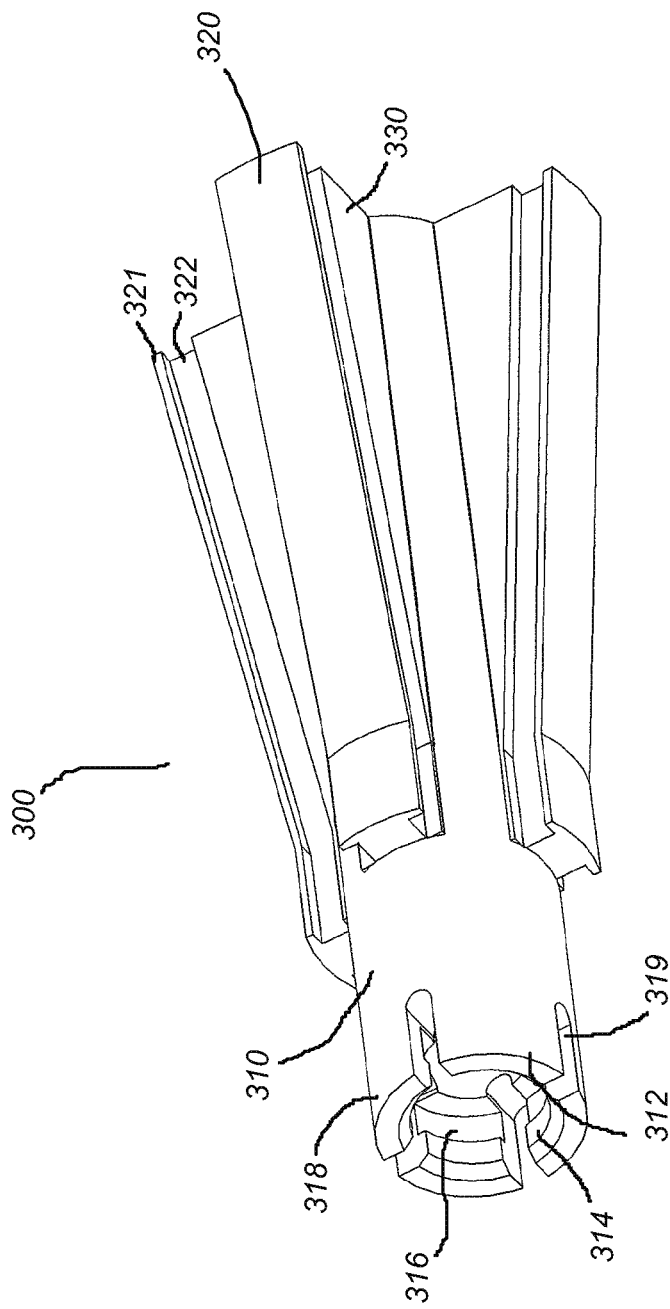
FIG. 3A shows a perspective proximal view of one embodiment of a spreader.
Figure 3B:
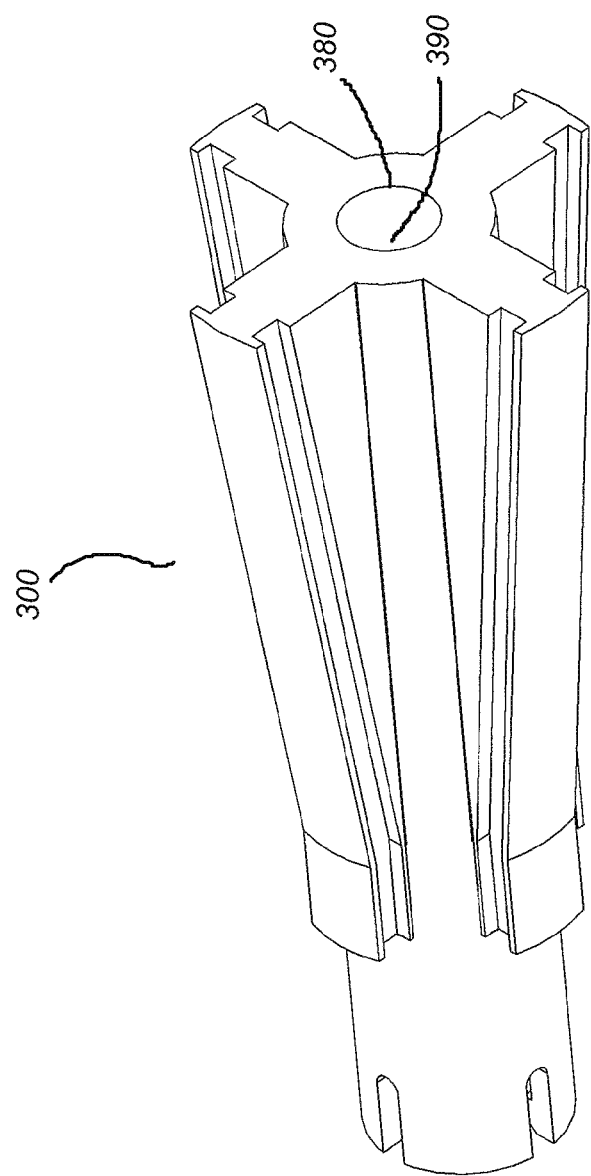
FIG. 3B shows a perspective distal view of one embodiment of a spreader.
Figure 3C:
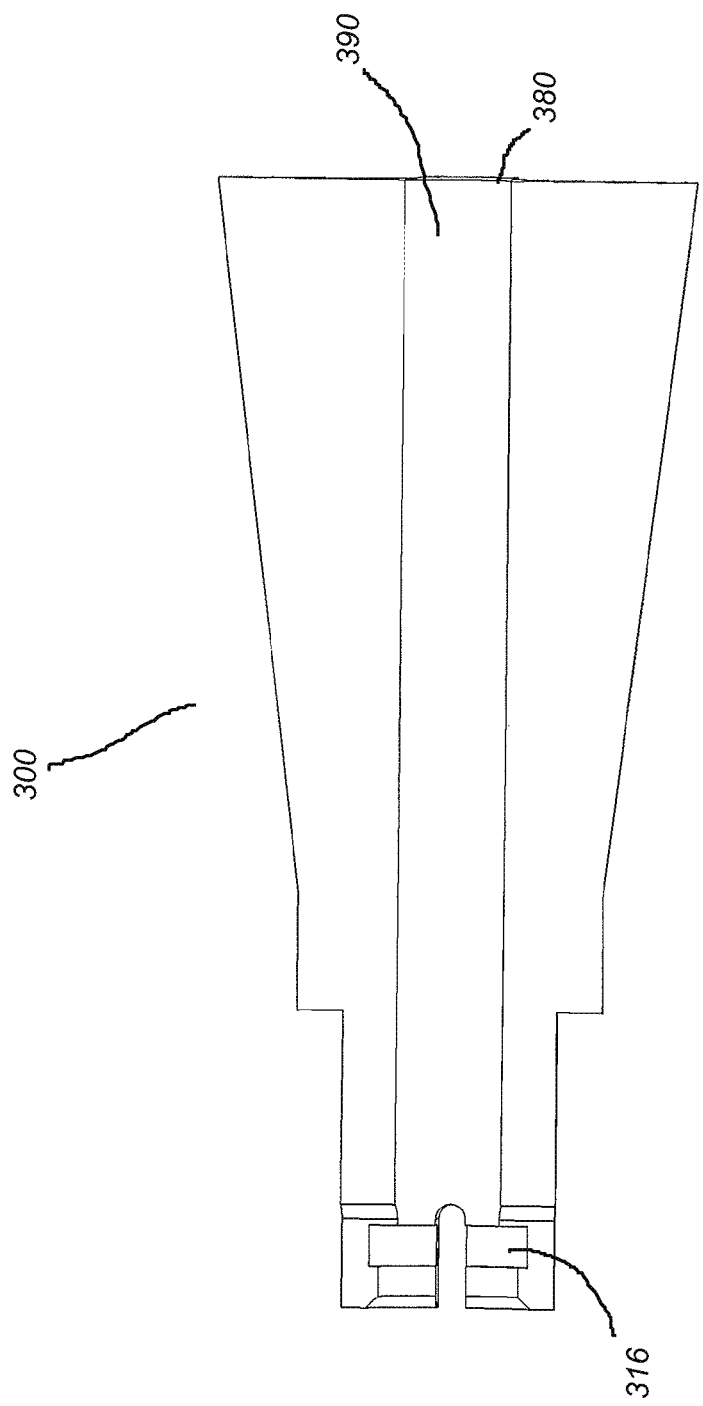
FIG. 3C shows a cross-sectional view of one embodiment of a spreader.

FIG. 3A shows a perspective proximal view of a spreader and FIG. 3B shows a perspective distal view, and FIG. 3C shows a cross-sectional view of the spreader. The spreader 300 of FIGS. 3A-3C has a substantially tubular body 310 with tracks 320 disposed on an outer surface 312 of the tubular body 310. The tracks 320 of some embodiments run longitudinally along the outer surface 312 from a distal portion of the spreader 300 to a proximal portion of the spreader 300. In some embodiments, the tracks 320 are complementary in placement and shape to the grooves 220 of the anchor body 200, and the tracks 320 are configured to fit within the grooves 220. The grooves 220 and the tracks 320 may include additional complementary features such as ridges 321, indentations 322, bumps 323, dimples, protrusions, recesses, and the like, designed to lock the track 320 within the groove 220. When the track 320 of the spreader 300 is locked within the groove 220 of the anchor body 200, axial displacement and rotation of the spreader 300 relative to the anchor body 200 is limited. Longitudinal displacement of the track 320 relative to the groove 220 is still possible in the locked position. It will be appreciated by those skilled in the art that in some embodiments, the complementary features can be reversed such that the anchor body 200 includes a set of tracks or protrusions and the spreader 300 includes a set of grooves or recesses.

In various embodiments, the tracks 320 are non-uniformly elevated from the outer surface 312 of the tubular body 310 along a length of the spreader 300. For example, in some embodiments, such as the embodiment of FIGS. 3A and 3B, each of the tracks 320 is disposed on a wedge-like projection 330 (hereinafter, a "wedge"), which extends radially outward from the tubular body 310. In various embodiments, the wedge 330 extends most radially outward at a proximal end of the spreader 300 and tapers radially inward in the distal direction.

Also shown in FIG. 3A is a depression 316 (e.g., a groove) circumferentially arranged along an inner surface 314 of the spreader 300 at the distal end of the spreader 300. The depression 316 is configured to engage with a portion of the distal tip 260, as described in more detail below. In some embodiments, the depression 316 is located on or within one or more bendable tabs 318. The bendable tabs 318 are defined by a plurality of cuts 319 made into a distal end of the tubular body 310. The bendable tabs are configured to bend outwardly, bending from a base of the cuts 319, when the spreader 300 makes contact with a distal tip 260 of the anchor body.

Additionally, as shown best in FIGS. 3B and 3C, in various embodiments, the spreader 300 has an opening 380 leading into an inner channel 390 configured to receive and couple to an insertion tool. One embodiment of an insertion tool 1000 is discussed in more detail below.

Figure 4:
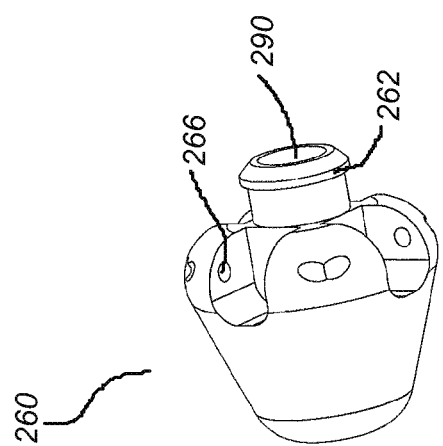
FIG. 4 shows a perspective view of one embodiment of a distal tip of an anchor body.

One embodiment of a distal tip 260 of an anchor body 200 is depicted in FIG. 4. In various distal tip embodiments, the distal tip is substantially closed and rounded to create a streamlined design. The shape of the distal tip 260 facilitates insertion of the anchor body 200 into a bone tunnel and helps the anchor body 200 slide around soft tissue positioned within the bone tunnel without causing injury to the tissue. A small hole 290 may advantageously be provided in the center of the distal tip 260 to facilitate engagement of the anchor body 200 with an insertion tool. The small hole 290 may be surrounded by threads configured to mate with threads on an inner rod of the insertion tool. In some embodiments, the distal tip 260 includes a lip 262 (e.g., a protruding ridge) configured engage the depression 316 of the spreader 300. Engagement between the depression 316 of the spreader 300 and the lip 262 of the distal tip 260 limits longitudinal movement of the spreader 300 and secures the tissue anchor device 100 in an expanded state. The anchor body tip may additionally include holes, pins, and or other features 266 for attaching the hinge element 225 to the distal tip 260 about a proximal pivot 226.

As shown in FIG. 5A, in various embodiments, the distal end of the spreader 300 is configured to enter the central bore 265 at a proximal end of the anchor body 200. In the provided illustration, the spreader 300 has entered the central bore, but has not been advanced substantially into the central bore; as a result, the panels 210 are still in an unexpanded position. The spreader 300 is configured to continue advancing distally deeper into the central bore by sliding within the grooves 220 of the anchor body 200. The spreader 300 is configured to urge the panels 210 of the anchor body 200 radially outward relative to the central bore 265 upon insertion of the spreader 300 into the central bore as shown in FIG. 5B, where the panels 210 are in an expanded position.

With the anchor body 200 and the spreader 300 aligned such that the tracks 320 of the spreader 300 are at least partially disposed within the grooves 220 of the anchor body 200, sliding the spreader 300 into the central bore causes the panels 210 to be displaced outward, following the taper of the spreader 300. This outward displacement causes the panels 210 to separate from each other and causes the anchor body 200 to expand. In various embodiments, the panels 210 are configured to engage with soft tissue and bone when the panels 210 are pivoted to an expanded position, fixedly securing the tissue anchoring device 100 and the soft tissue within a bone tunnel. As shown in FIG. 5B, in various embodiments, the entire length of each panel 210 is displaced outwardly when the panels 210 are in an expanded position. The outward displacement is possible due to pivoting about the proximal pivot 226 and the distal pivot 224.

In some embodiments, distal movement of the spreader 300 within the anchor body 200 leads primarily to pivoting about the proximal pivot 226 as the panels 210 are urged further outward by the increasing diameter of the advancing wedge 330. In some such embodiments, the spreader 300 can be inserted into the central bore of the anchor body 200 until the depression 316 of the spreader 300 engages with the lip 262 of the distal tip 260 (as shown in FIG. 3C and FIG. 4, respectively). Upon engagement of the lip 262 with the depression 316, contact is made between the distal end of the spreader 300 and the hinge elements 225, and a force is applied to the hinge elements 225, urging them to swing radially outward and pivot about the distal pivot 224. The panels 210 transition to a fully expanded position when the hinge element 225 swings outward about the distal pivot 224. In such an expanded position, the panels 210 extend radially outward from the anchor body 200. In some embodiments, each panel 210 undergoes relatively uniform expansion along the length of the panel 210. In other embodiments, as depicted in FIG. 5B, the panels 210 expand to a greater extent at their proximal end as compared to their distal end.

In embodiments described herein, the outward displacement of the panels 210 and resultant expansion of the anchor body 200 is achieved without the need for applying any torque to the tissue anchoring device 100. Thus, advantageously, insertion and expansion of the tissue anchoring devices 100 disclosed herein is likely to prevent any twisting or turning of the soft tissue within a bone tunnel.

In various embodiments, the tissue anchoring device 100 is inserted into a bone tunnel with the aid of an inserter tool, for example, inserter tool 3000. More details about insertion tool 3000 are provided below.

Figure 6A:
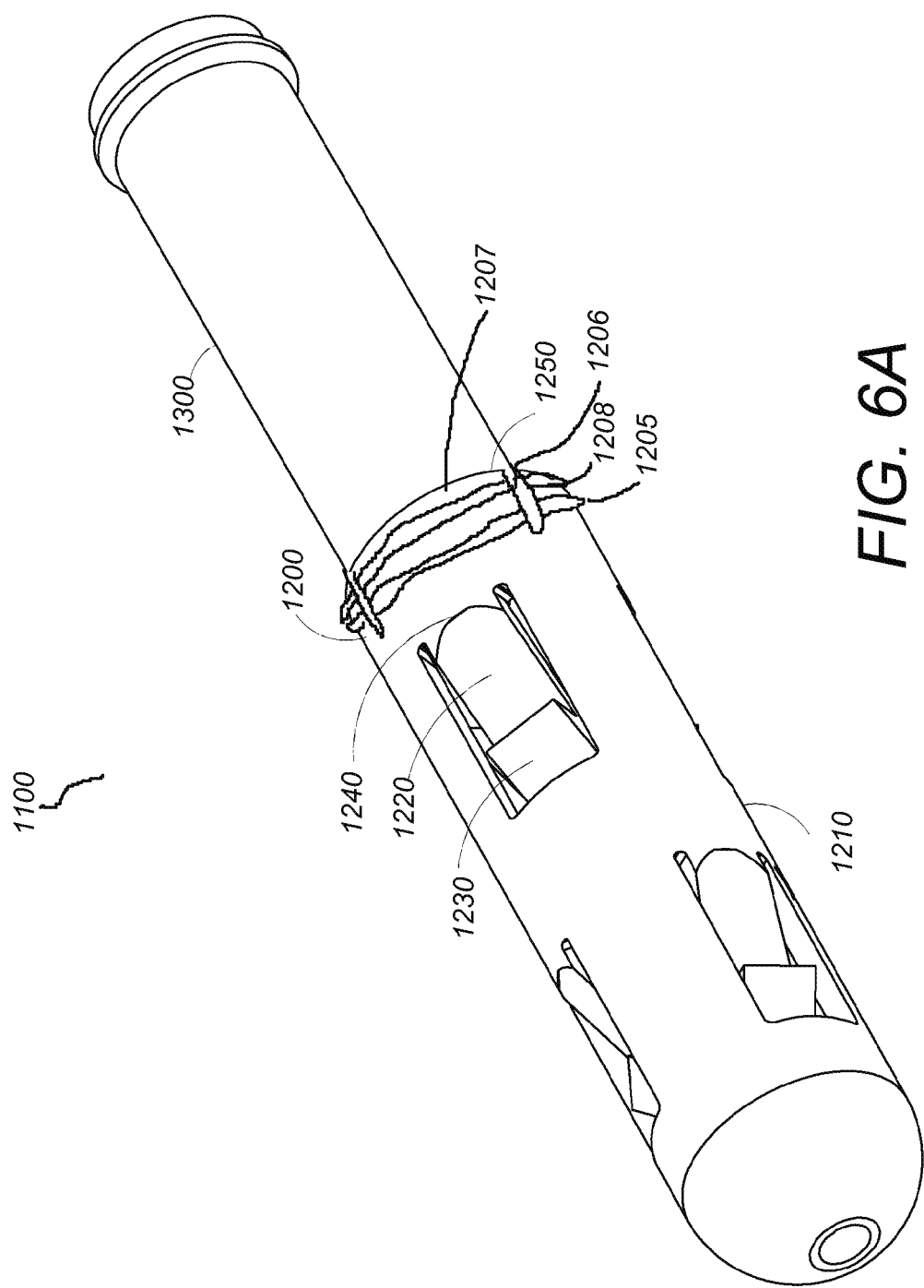
FIG. 6A shows a perspective view of one embodiment of a tissue anchoring device in an unexpanded/undeployed state.

Another embodiment of a tissue anchoring device 1100 is depicted in FIG. 6A. The anchor body 1200 is comprised of a tubular wall 1210 defining a central bore and having compressible tabs 1220. In one embodiment the tubular wall 1210 is uniformly tubular in that it comprises a uniform diameter. The compressible tabs 1220 are configured to engage with soft tissue and bone, fixedly securing the anchor body 1200 and the soft tissue in the bone. In some embodiments, the compressible tabs comprise one or more teeth 1230 which are configured to further engage with the tissue and bone. The number of compressible tabs 1220 and teeth 1230 can vary. The compressible tabs are affixed to the tubular wall along an edge 1240. The edge 1240 is configured to allow pivotal movement about the tubular wall such that the compressible tabs are bendable between a compressed state and an expanded state. The tissue anchoring device also comprises a spreader 1300, which is insertable into the central bore at the anchor body's proximal end 1250 and configured to urge the compressible tabs 1220 radially outward relative to the tubular wall 1210 upon insertion of the spreader into the central bore. In FIG. 6A, the spreader 1300 is in its undeployed or uninserted state such that the compressible tabs 1220 are collapsed and in their compressible state. In the embodiment depicted in FIG. 6A, when the compressible tabs 1220 are in their compressed state, the tissue anchoring device 1100 is in a streamlined position such that there is little to no protrusion of the teeth 1230 radially outward beyond the tubular wall.

In the tissue anchoring device embodiment of FIG. 6A, the tissue anchoring device 1100 also includes a proximal-most portion 1205, which is outwardly expandable. Expansion slots 1206 are cut into the anchor body 1200 at the proximal end and extend in a distal direction such that the outwardly expandable proximal portion 1205 comprises a plurality of expandable segments 1207 that are disconnected from each other. Each expandable segment 1207 is connected to the remainder of the anchor body 1200 (i.e., to a non-expanding distal portion of the anchor body 200) at a distal end of each respective expandable segment 1207. In the depicted embodiment, the expandable segments 1207 are configured to bend radially outward when the spreader 1300 is fully advanced distally into the central bore 1265 of the anchor body 1200. In some embodiments, contact between an inner surface of the anchor body 1200 and a ridge 1325 of the spreader 1300 creates a force that urges the expandable segments 1207 radially outward.

In some embodiments, the tissue anchor 1100 is configured such that, when the tissue anchor 1100 is placed in a properly-sized bone hole, the outwardly expandable proximal-most portion 1205 is positioned within the cortical layer of bone near the aperture of a bone tunnel. In such embodiments, the expandable segments 1207 may be tailored to expand into the cortical layer and provide for cortical fixation. In other embodiments, the expandable segments 1207 may be configured for cortical and subcortical engagement. In various embodiments, each expandable segment 1207 has a sharp edge, one or more ridges, teeth, or other protrusions 1208, which facilitate engagement of the expandable segment 1207 with surrounding bone.

Figure 6B:
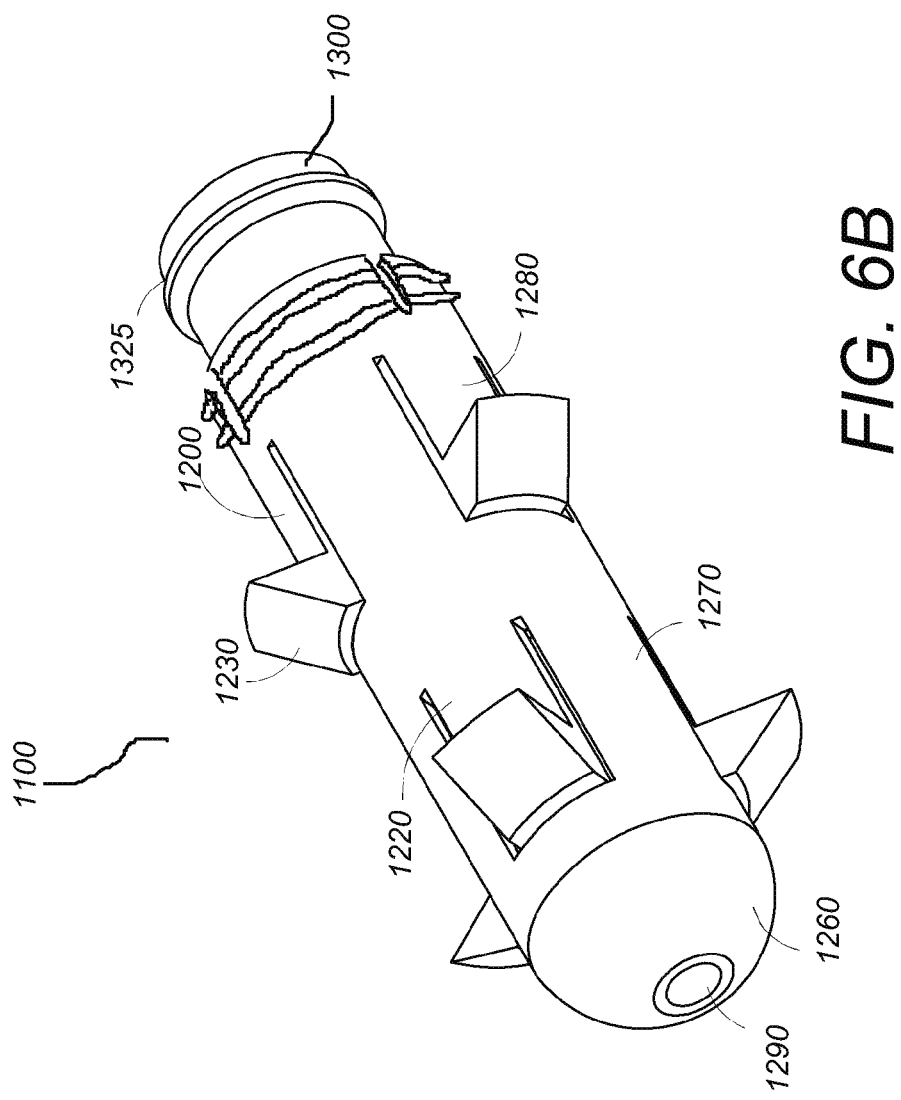
FIG. 6B shows a perspective view of one embodiment of a tissue anchoring device in an expanded/deployed state.

One embodiment of the tissue anchoring device is also depicted in FIG. 6B. FIG. 6B shows a perspective view in which the spreader 1300 has been inserted into the central bore of the anchor body 1200, thus moving the compressible tabs 1220 into their expanded state. In such an expanded state, the teeth 1230 extend radially outward from the anchor body 1200 and are configured to engage with bone and fixedly secure the tissue anchoring device 1100 within the bone. In the embodiment of FIG. 6B, the compressible tabs are positioned along circumferential rows. A first row 1270 contains compressible tabs located along a first axial position, and a second row 1280 contains compressible tabs located along a second axial position. In some embodiments, the first row of tabs 1270 is offset circumferentially relative to the second row of tabs 1280 such that no two compressible tabs 1220 share the same longitudinal alignment. Such a configuration facilitates capture and fixation of a soft tissue by hindering slippage of the soft tissue between the compressible tabs.

Figure 6C:
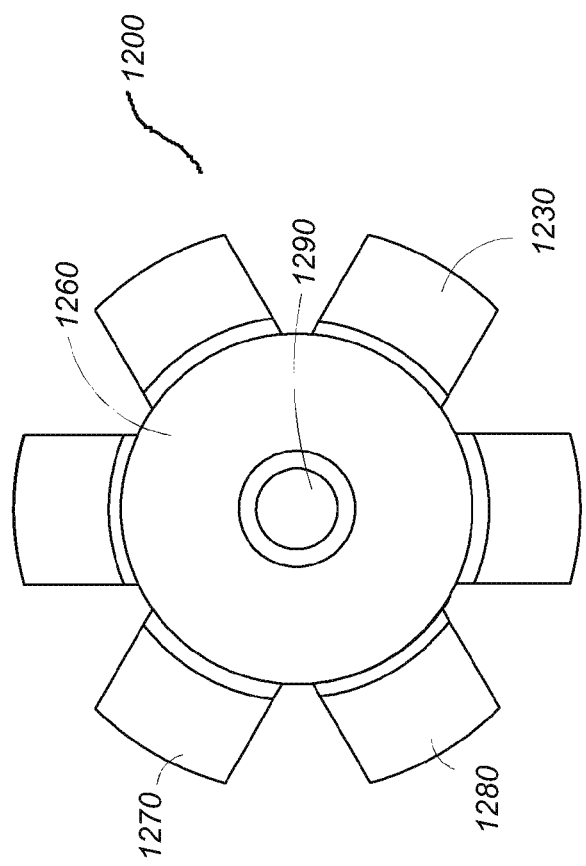
FIG. 6C shows a front view of one embodiment of a tissue anchoring device in the expanded/deployed state.

FIG. 6C provides a front view of the embodiment described in FIG. 6B. FIG. 6C depicts compressible tabs 1230 in their expanded state and a first row of compressible tabs 1270 offset circumferentially from a second row of compressible tabs 1280.

In some embodiments, the distal end 1260 of the anchor body is substantially rounded to facilitate insertion of the anchor body into a bone tunnel and to slide around tendon positioned within the bone tunnel. A small hole 1290 may advantageously be provided in the center of the distal end 1260 to facilitate engagement of the anchor body with an insertion tool, such insertion tool explained in subsequent paragraphs. The small hole 1290 may comprise threads to mate with the threads on the inner rod of the insertion tool.

Figure 7A:
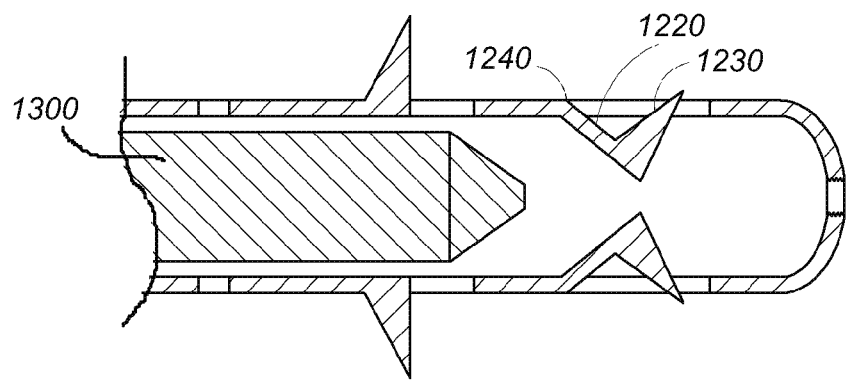
FIG. 7A shows a cross-sectional view of one embodiment of a tissue anchoring device in which the tissue anchoring device has partially deployed or expanded.

In one embodiment of the tissue anchoring device, a plurality of compressible tabs are located along the same axial position, forming circumferential rows of compressible tabs. As shown in the cross-sectional view of FIG. 7A, the compressible tabs move about a hinge-like edge 1240, moving from a compressed state to an expanded state upon insertion of the spreader 1300 through the proximal end 1250 of the anchor body and into the central bore. In the expanded state, the compressible tabs 1220 are substantially flush with the tubular wall and the teeth 1230 protrude radially outwardly relative to the anchor body.

Figure 7B:
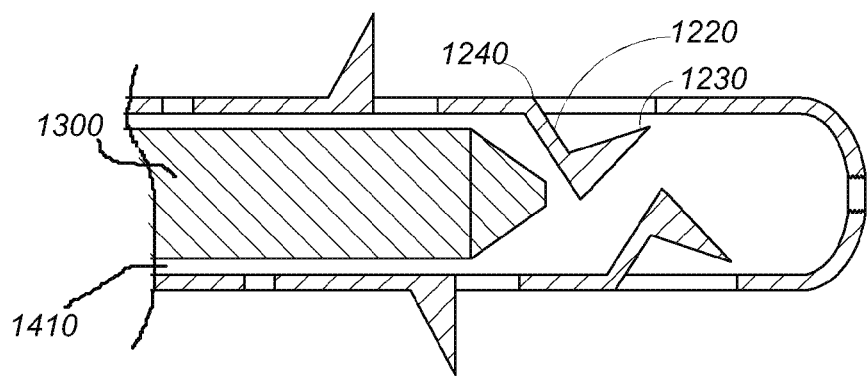
FIG. 7B shows a cross-sectional view of another embodiment of a tissue anchoring device in which the tissue anchoring device has partially deployed or expanded.

In another embodiment of the tissue anchoring device, there exists a plurality of compressible tabs 1220, wherein all compressible tabs are offset axially relative to one another. FIG. 7B depicts a cross-sectional view of such an embodiment. With the compressible tabs 1220 offset axially, such that no two tabs lie along the same axial position, each tab can be configured to extend beyond the center line or central axis of the central bore when the tab is in its compressed state. Such a configuration allows for the inclusion of larger teeth 1230 on the compressible tab than would be possible with many other embodiments, thus facilitating increased contact between the teeth and bone.

Figure 8A:
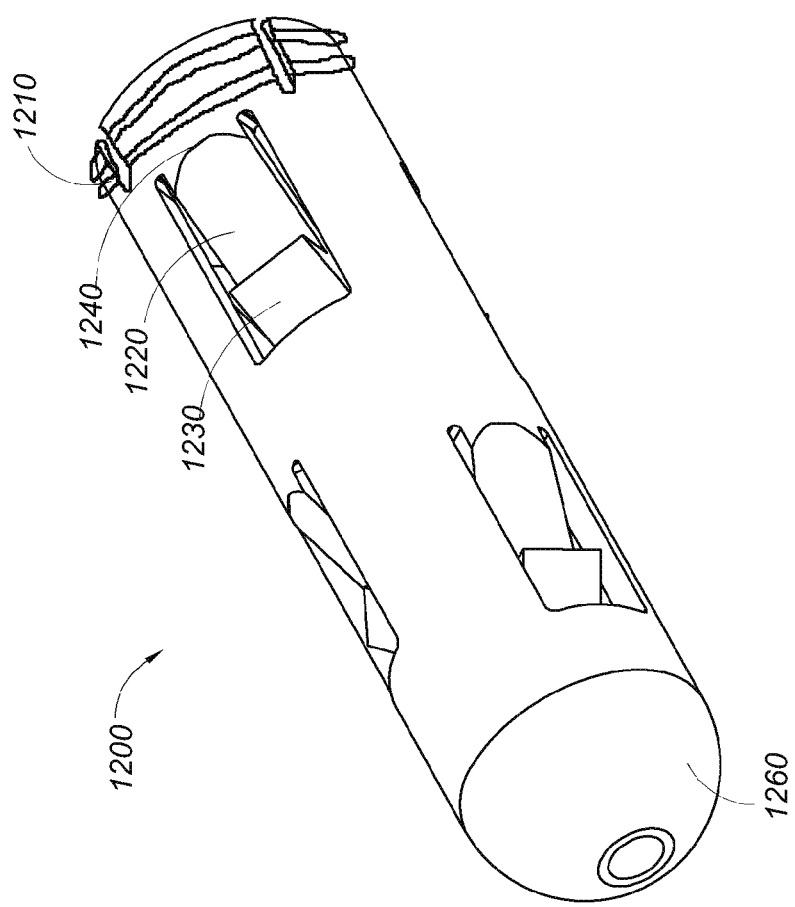
FIG. 8A depicts a perspective distal view of one embodiment of an anchor body in an unexpanded/undeployed state.

One embodiment, described in the preceding paragraph, is further illustrated in the perspective view provided in FIG. 8A. In FIG. 8A, the anchor body 1200 is shown in isolation with the compressible tabs 1220 found in their compressed or undeployed state. The anchor body 1200 is generally tubular or cylindrical in shape and is comprised of a uniform diameter. The compressible tabs 1220 bend inward along the bendable edge 1240 such that the teeth 1230 are largely retracted into the central bore inside the anchor body and do not extend substantially beyond the tubular wall 1210 prior to insertion of the spreader. The compressible tabs 1220 are offset both axially and circumferentially relative to each other.

Figure 8B:
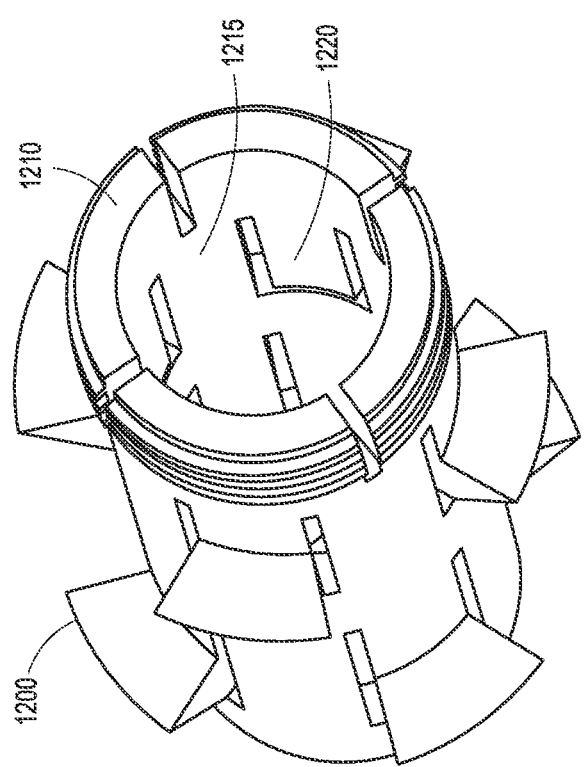
FIG. 8B depicts a perspective proximal view of one embodiment of an anchor body in an unexpanded/undeployed state.

Another embodiment of a compressed or undeployed anchor body is shown in the perspective view of FIG. 8B. In FIG. 8B, the central bore defined by the tubular wall 1210 is visible from the proximal side of the anchor body. The anchor body of this embodiment has an inner surface 1215 of the tubular wall which is in contact with a spreader 1300 when the spreader is inserted into the anchor body. In some embodiments, the inner surface 1215 may be smooth. In other embodiments, in inner surface 1215 of the anchor body and the surface of the spreader 1300 may not be smooth, but rather, may be textured such as with a scallop shape or grooves so as to inhibit movement of spreader 1300 once it is pushed into the anchor body. In some embodiments, texturing in the inner surface 1215 is complementary to texturing in the outer surface of the spreader 1300. Such a design prevents unintended retraction or over-insertion of the spreader. In some embodiments, one or more complementary shapes, including multiple concentric grooves, a series of protruding ridges, or any other suitable complementary structures may be present on the inner surface 1215 of the anchor body 1200 and an outer surface of the spreader 1300 to lock the spreader 1300 into place when the anchor body 1200 is fully deployed in order to prevent unintended retraction or over-insertion of the spreader 1300.

Figure 9A:
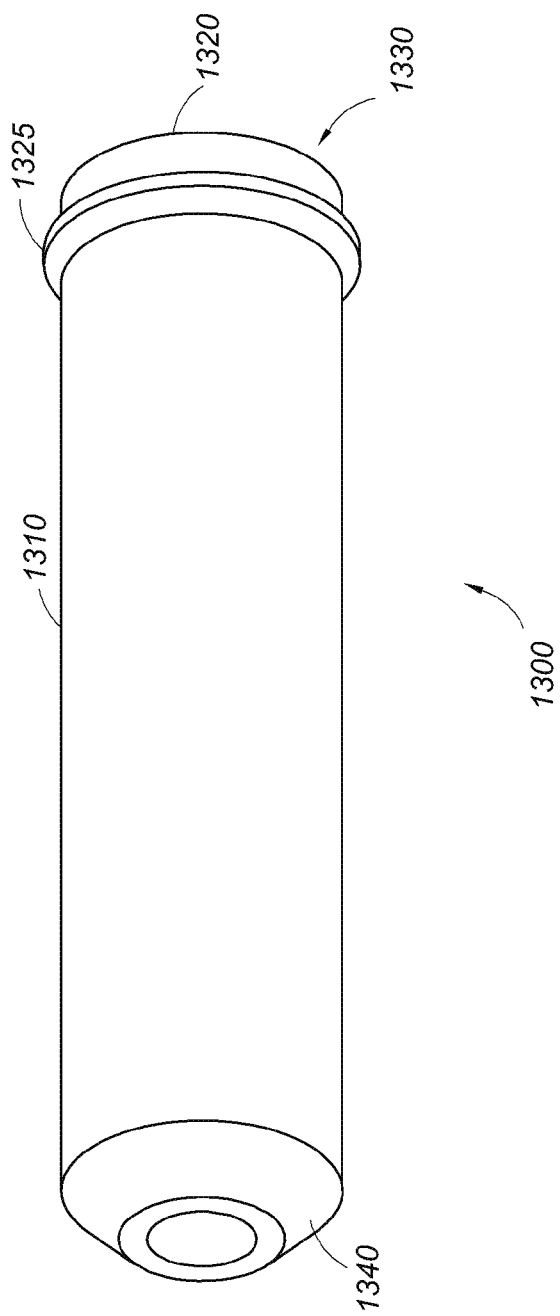
FIG. 9A depicts a perspective distal view of one embodiment of a spreader.
Figure 9B:
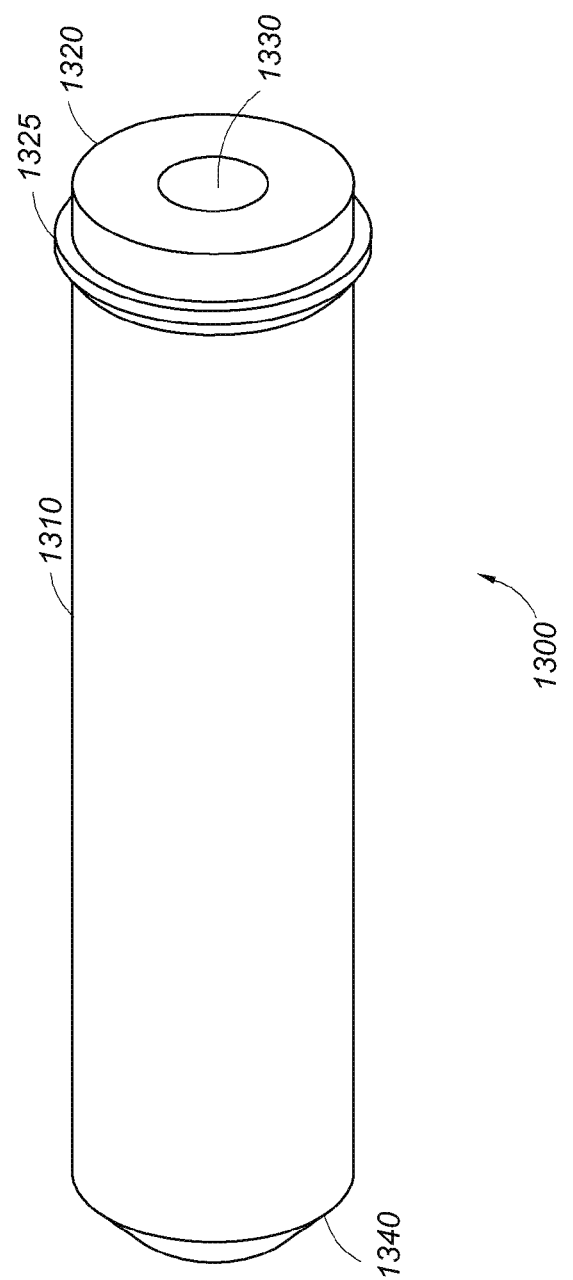
FIG. 9B depicts a perspective proximal view of one embodiment of a spreader.

To provide further details of the spreader, an embodiment of the spreader is depicted in FIGS. 9A and 9B. The spreader 1300 may comprise any suitable shape configured to be inserted through the central bore of the anchor body 1200. In the embodiment of FIGS. 9A and 9B, the generally tapered distal end 1340 of the spreader is configured to come into contact with the compressible tabs of the anchor body and facilitate bending of the tabs into their expanded state upon insertion of the spreader into the anchor body. The body 1310 of the spreader is uniformly tubularly shaped and surrounds an axial bore configured for receiving an insertion tool. In this embodiment, the tubular body 1310 of the spreader 1300 comprises a circumferentially located ridge 1325 near its proximal end 1320. As the tissue anchoring device is deployed, the spreader 1300 is advanced into the anchor body 1200, spreading the compressible tabs 1220 until the ridge 1325 of the spreader 1300 engages the groove 1225 in the inner surface of the anchor body. In one embodiment, the ridge 1315 may be undercut providing even more security against reversing. The proximal end of the spreader comprises a generally flat face and a means for receiving the insertion tool. For instance, in this embodiment, the proximal end 1320 of the spreader 1300 comprises a hole 1330 that receives the insertion tool. After deployment, the spreader remains in the deployed anchor and the insertion tool's inner rod shears off from the anchor body such that the proximal end of the spreader 1300 remains in the anchor in a state that is either flush or slightly recessed with respect to the proximal end of the anchor body 1200.

The spreader 1300 will remain in the anchor body 1200 with the compressible tabs 1220 in their fully expanded position. The force provided by the interaction between the compressible tabs, teeth and bone keeps the spreader 1300 tightly engaged. Further protection against slipping or tilting of the spreader 1300 is provided by the optionally ridged sides of the spreader 1300. In one embodiment, one or more of the compressible tabs 1220 have an indentation on a side facing the central bore. A ridge on the spreader 1300 can then engage the indentation, thereby stabilizing the spreader 1300 and preventing the spreader 1300 from being advanced too far into the anchor. In an alternative embodiment, the spreader 1300 comprises an indentation that can engage with a protrusion on a side of a compressible tab facing the central bore. In addition to stabilizing the spreader 1300 and preventing over-insertion, this feature also prevents rotation of the spreader 1300 relative to the anchor. Inserting the spreader 1300 into the anchor body 1200 linearly, as opposed to twisting or screwing, is likely to be advantageous in that the linear motion will create no tendency to rotate the anchor. Thus, a linear approach is likely to prevent any twisting or turning of the captured soft tissue.

Figure 10A:
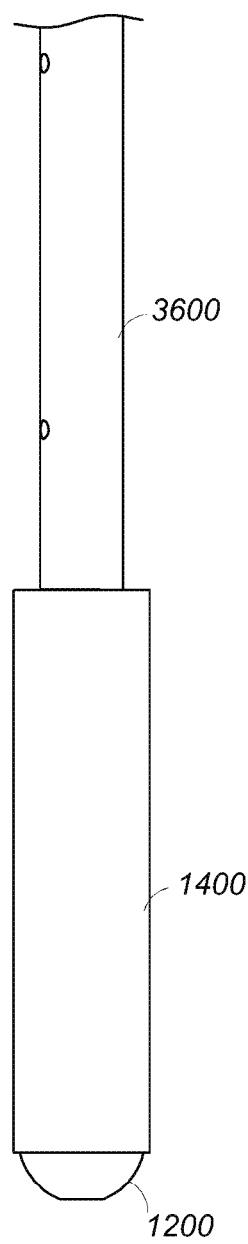
FIG. 10A depicts a side view of one embodiment of a tissue anchoring device attached to an inserter tool and covered by a sleeve.
Figure 10B:
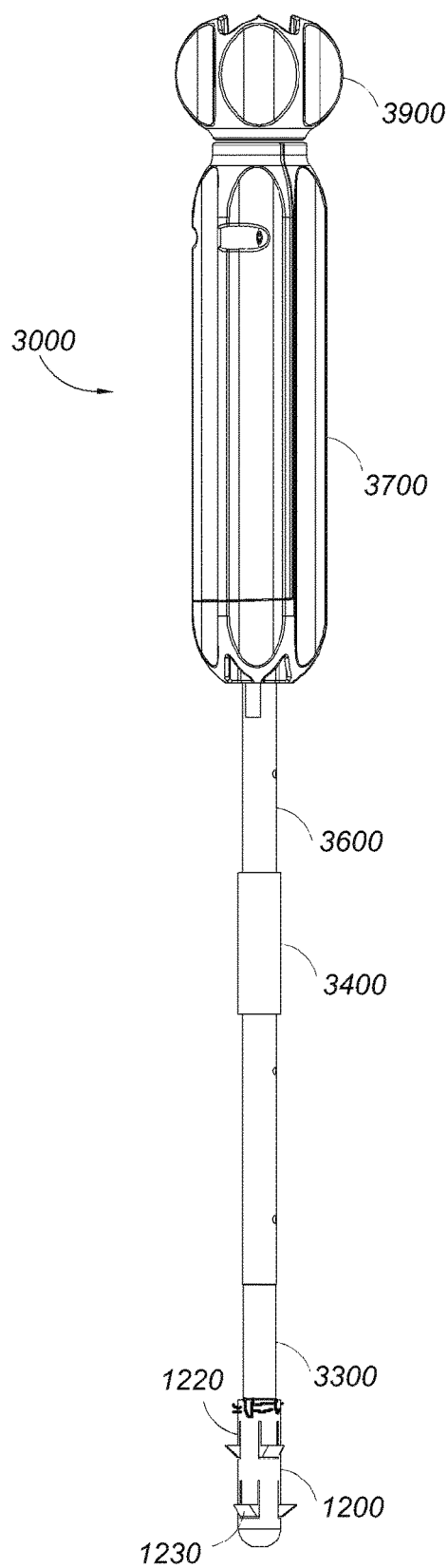
FIG. 10B depicts a perspective view of one embodiment of a tissue anchoring device attached to an inserter tool with the sleeve retracted.

In one embodiment, illustrated in FIGS. 10A and 10B, the compressible tabs may be of a thin enough material thickness such that they can be pushed in by a slidable sleeve 1400 positioned over the anchor body 1200. The slidable sleeve 1400 is configured to hold the compressible tabs 1220 in place substantially inside the anchor body 1200 during insertion of the anchor body 1200 into the bone tunnel. FIG. 10A shows one embodiment of the anchor body 1200 and slidable sleeve 1400 combination with the anchor body 1200 in its compressed state and with the combination connected to the outer tube 1600 of the insertion tool. The slidable sleeve 1400 can be withdrawn when the anchor body 1200 is in place inside a bone, and the compressible tabs will at least partially expand. The compressible tabs and teeth will completely expand according to the method described herein upon insertion of the spreader 1300 using the insertion tool 3000. FIG. 10B depicts one embodiment of the anchor body 1200 and slidable sleeve combination with the slidable sleeve 1400 in a retracted state such that the compressible tabs 1220 of the anchor body 1200 have partially expanded and the teeth 1230 partially protrude radially outward from the tubular wall. In this depiction, the spreader 1300 is held adjacent to the anchor body 1200 via the inserter tool 3000 prior to insertion of the inserter into the anchor body 1200.

Figure 11:
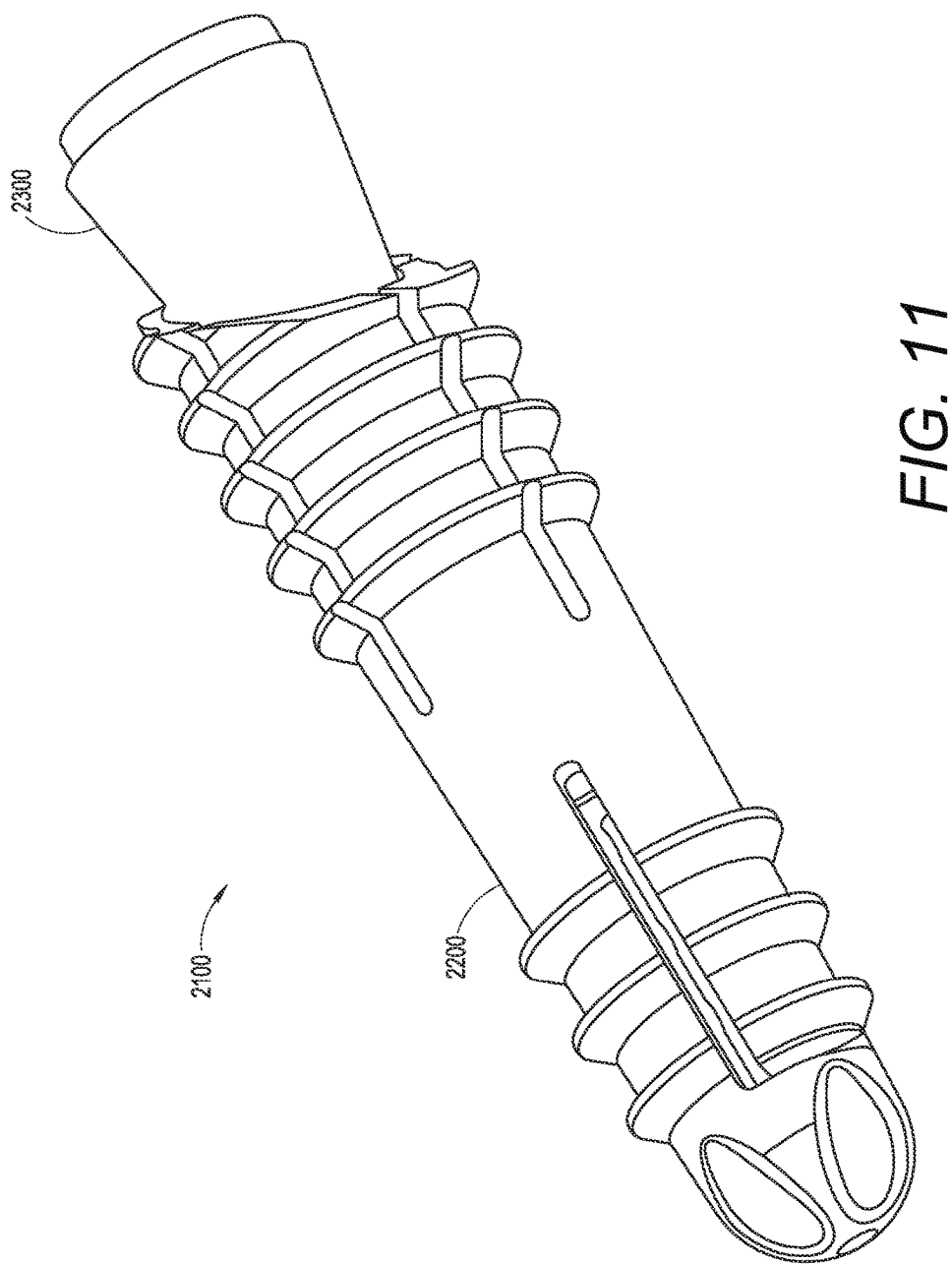
FIG. 11 depicts a perspective distal view of one embodiment of a tissue anchoring device in an unexpanded/undeployed state.

An additional embodiment of a tissue anchoring device 2100 in provided in FIGS. 11-14. Similar to the tissue anchoring device 1100 embodiment described above, the tissue anchoring device 2100 embodiment of FIG. 11 is comprised of an anchor body 2200 and a spreader 2300. The spreader 2300 is configured to slide or advance into a central bore 2265 of the anchor body 2200 without the need for applying torque.

Figure 12:
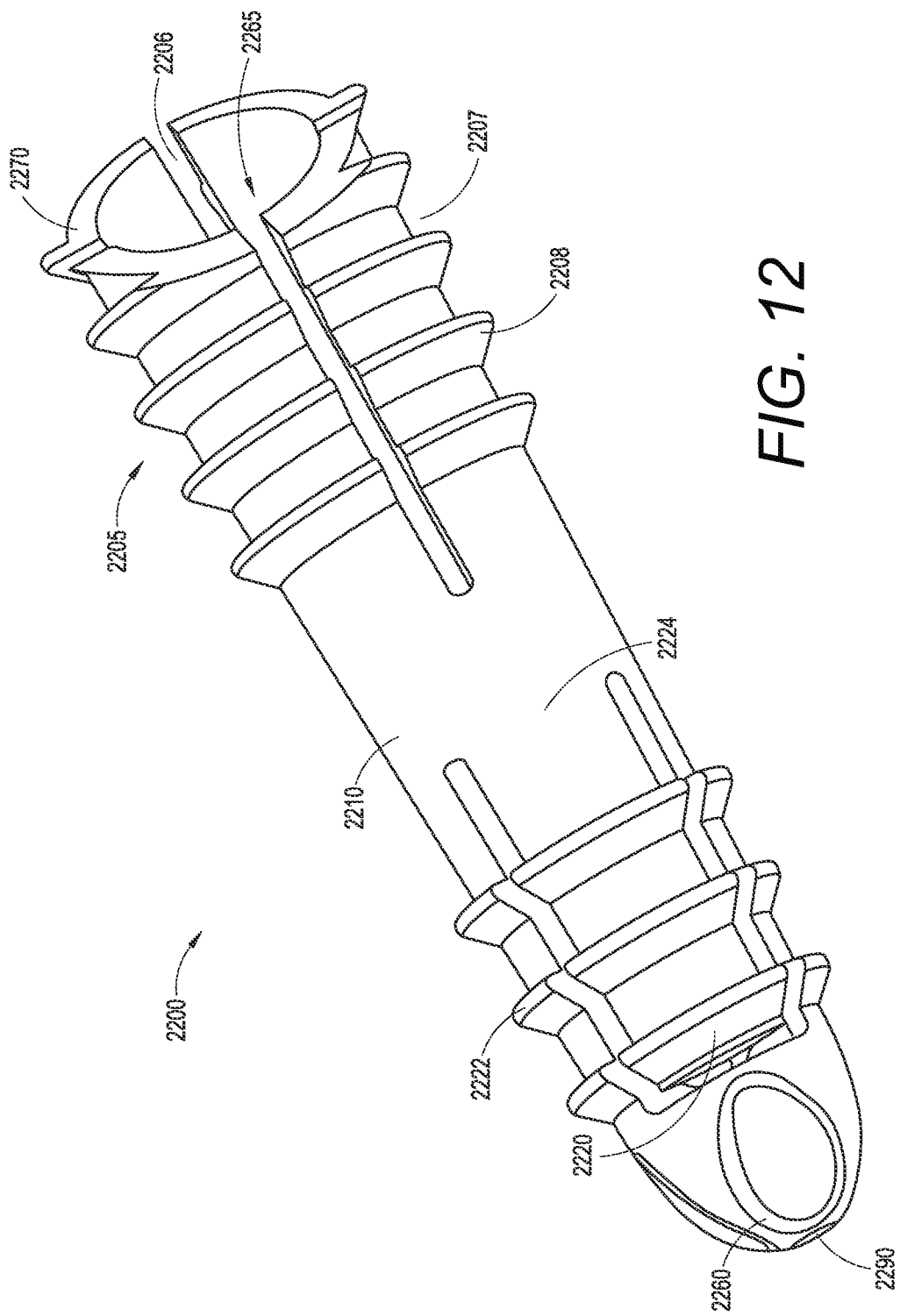
FIG. 12 depicts a perspective distal view of one embodiment of an anchoring body in an unexpanded/undeployed state.

As shown in FIG. 12, in some embodiments, the anchor body 2200 comprises a tubular wall 2210 defining a central bore 2265. In one embodiment the tubular wall 2210 is uniformly tubular in that it comprises a uniform diameter. In other embodiments, the tubular wall 2210 is tapered such that a distal diameter is smaller than a proximal diameter. The taper of some embodiments facilitates insertion of the tissue anchoring device 2100 into a bone tunnel. In some embodiments, the distal end 2260 of the anchor body 2200 is substantially rounded to facilitate insertion of the anchor body into a bone tunnel and to slide around tendon positioned within the bone tunnel. A small hole 2290 may be provided in the center of the distal end 2260 to facilitate engagement of the anchor body with an insertion tool, such insertion tool explained in subsequent paragraphs. The small hole 2290 may comprise threads to mate with the threads on the inner rod of the insertion tool. In some embodiments, the proximal end 2270 of the anchor body 2200 is cut on a slant, such that one side of the tubular anchor body extends longitudinally beyond another side of the tubular anchor body. Such a slant may be included on the proximal end 2270 when used in a bone tunnel having a slanted aperture at the entrance of the bone tunnel. Such a configuration may enable the proximal end 2270 of the anchor body 2200 to sit flush with a bone surface when a bone tunnel is drilled into a bone on an angle, as is often done.

The anchor body 2200 of FIG. 12 also includes a proximal portion 2205 that is outwardly expandable. As described in the previous anchor body 1200 embodiment, expansion slots 2206 are cut into the anchor body 2200 at the proximal end and extend in a distal direction such that the outwardly expandable proximal portion 2205 comprises a plurality of expandable segments 2207 (i.e., expandable side portions) that are disconnected from each other. Each expandable segment 2207 is connected to the remainder of the anchor body 2200 (i.e., to a non-expanding distal portion of the anchor body 2200) at a distal end of each respective expandable segment 2207. The expandable segments 2207 are configured to bend radially outward when the spreader 2300 is fully advanced distally into the central bore 2265 of the anchor body 2200. In some embodiments, the tissue anchor 2100 is configured such that, when the tissue anchor 2100 is placed in a properly-sized bone hole, the outwardly expandable proximal-most portion 2205 is positioned within the cortical layer of bone near the aperture of a bone tunnel. The expandable segments 2207 may be configured for cortical and/or subcortical engagement. In various embodiments, each expandable segment 2207 has a sharp edge, one or more ridges, teeth, or other protrusions 2208, which facilitate engagement of the expandable segment 2207 with surrounding bone.

Also shown in FIG. 12, in some embodiments, the anchor body 2200 has a plurality of expandable segments 2220 (i.e., expandable side portions) located on a more distal half of the anchor body 2200. The expandable segments 2220 are configured to be displaced radially outwardly (e.g., bend outwardly) when a spreader is inserted into the central bore 2265 of the anchor body 2200. The expandable segments are configured to engage with soft tissue and bone, fixedly securing the anchor body 2200 and the soft tissue in the bone. In some embodiments, the expandable segments 2220 comprise one or more protrusions 2222 (teeth, ridges, etc.) which are configured to further engage with the tissue and bone. The number of expandable segments 2220 and teeth 2222 can vary. The expandable segments 2220 are affixed to the tubular wall along an edge 2224. The edge 2224 is configured to allow pivotal movement about the tubular wall 2210 such that the tines 2222 are bendable between a compressed state and an expanded state. In some embodiments, such as that shown in FIG. 12, the expandable segments 2220 and edges 2224 are oriented and configured such that upon expansion, a distal end of the expandable segments 2220 experiences the greatest displacement.

Figure 13:
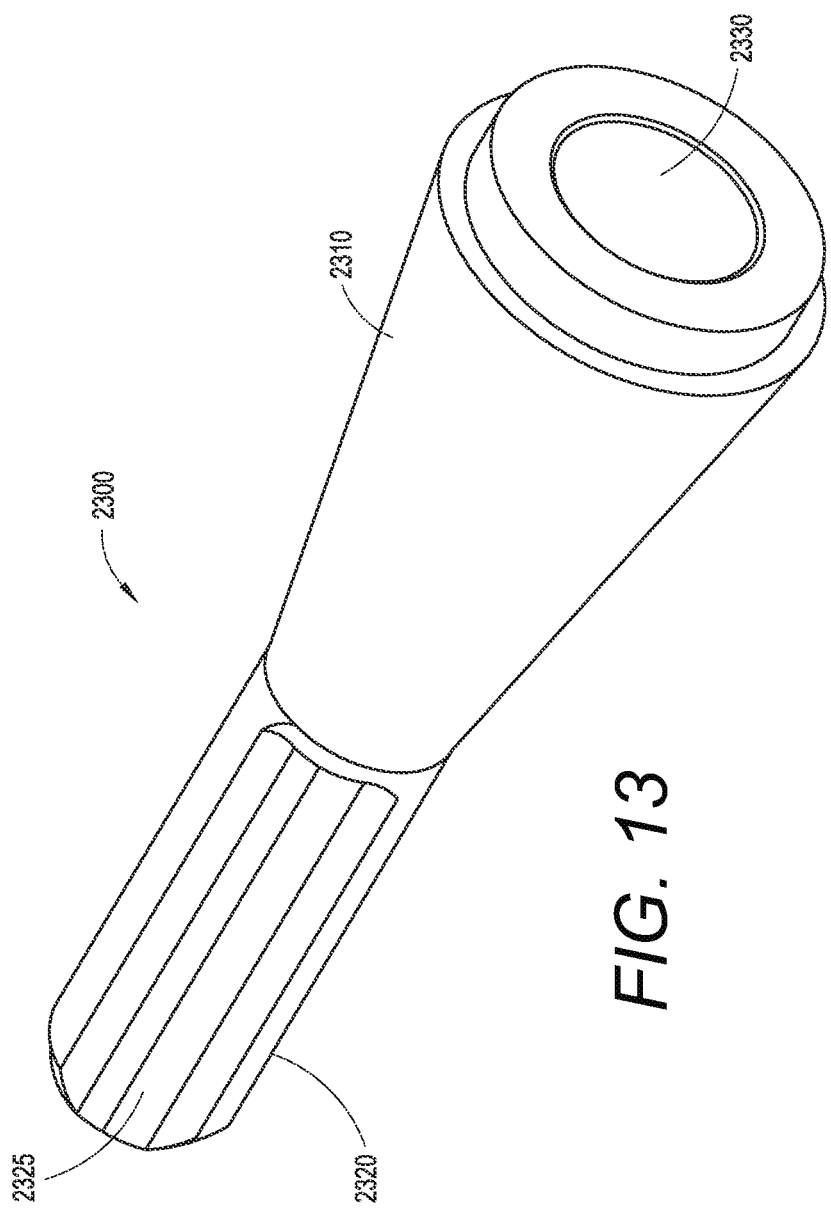
FIG. 13 depicts a perspective proximal view of one embodiment of a spreader.

FIG. 13 depicts the spreader 2300 of the tissue anchoring device 2100. In some embodiments, the spreader 2300 includes a conical portion 2310 and a tubular portion 2320. In other embodiments, the spreader 2300 is entirely tubular or conical. In some embodiments, a flattened, grooved portion 2325, or similar feature, is present on an outer surface of the spreader 2300 to complement a feature within the central bore 2265 of the anchor body 2200, and thus align the orientation of the spreader 2300 within the bore 2265. Such alignment features restrict axial and rotational movement of the spreader 2300. The spreader 2300 of various embodiments also includes a hole 2330 for receiving an insertion tool.

Figure 14:
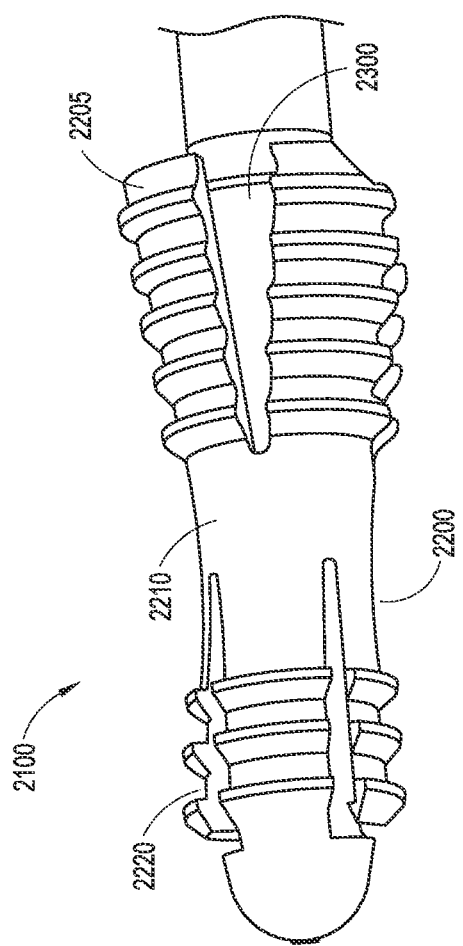
FIG. 14 depicts a perspective distal view of one embodiment of a tissue anchoring device in an expanded/deployed state.

FIG. 14 depicts the tissue anchoring device 2100 in an expanded state. As in other embodiments, the spreader 2300 is insertable into the central bore 2265 at the proximal end of the anchor body 2200 and configured to urge the expandable segments 2220 and expandable proximal portion 2205 radially outward relative to the tubular wall 2210 upon insertion of the spreader 2300 into the central bore. Such radial expansion on both a proximal portion and a distal portion allows for improved fixation of the tissue anchoring device 2100, including fixation within a proximal aperture of a bone tunnel and a distal aperture of the bone tunnel.

In various embodiments of the tissue anchoring devices disclosed herein, the tissue anchoring device is made entirely of a biocompatible engineering plastic. Other embodiments include a tissue anchoring device made entirely, or in part, of a biocompatible non-metallic substance. Biocompatible engineering polymer materials such as polyether-ether-ketone, poly-ether-ketone, polyetherimide, ultrahigh molecular weight polyethylene, polyphenylene, poly(lactide-co-glycolide), polycaprolactone, or some other biocompatible polymer material known to those of skill in the art may be used. A non-metallic anchor system may provide certain advantages such as, for example, eliminating MRI artifacts.

Figure 15A:
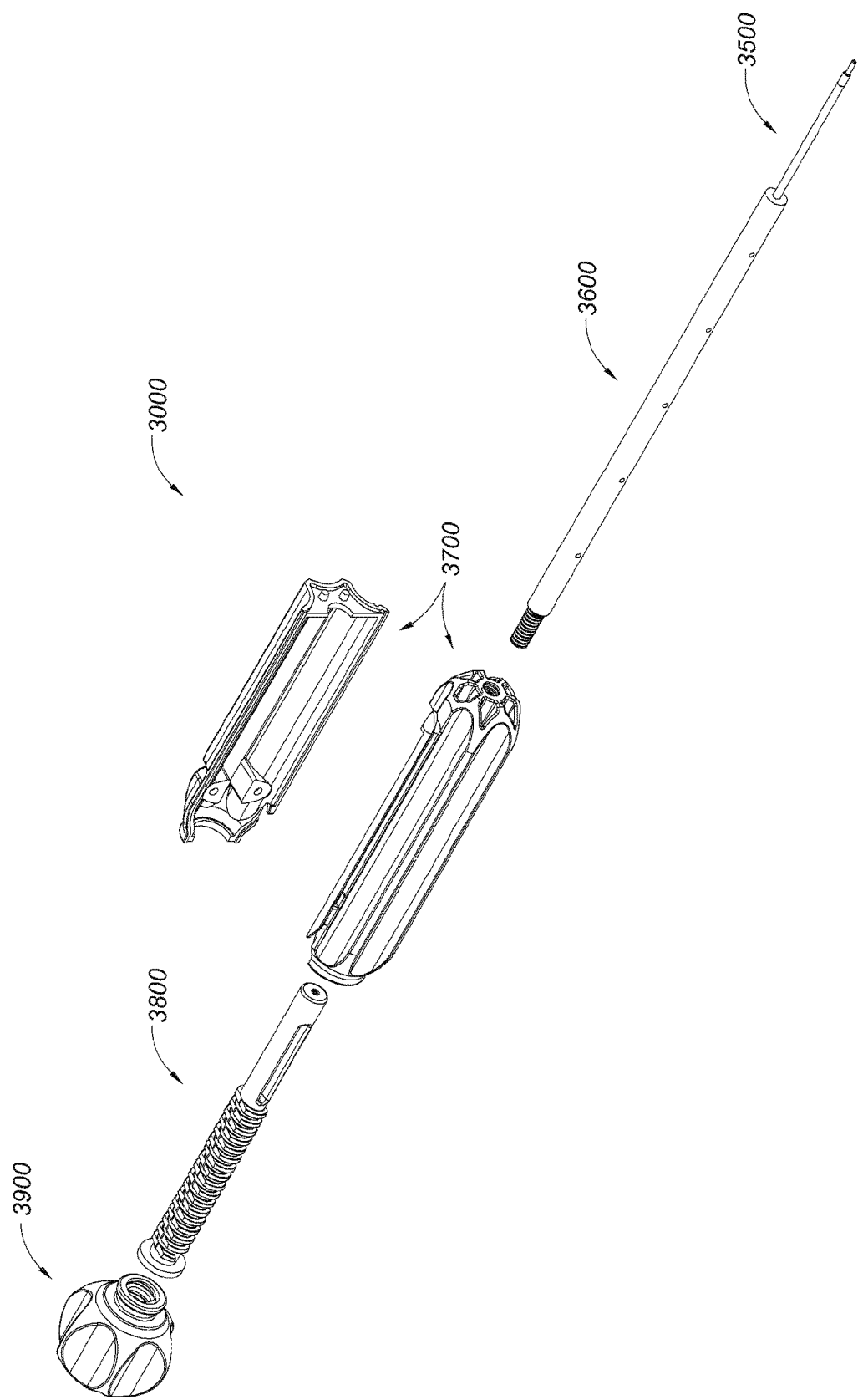
FIG. 15A shows an exploded view of one embodiment of an inserter tool.

FIG. 15A depicts individual components of an inserter tool, which may, in some embodiments, be used with any tissue anchoring device design disclosed herein. The inserter tool 3000 comprises an inner rod or tube 3500, an outer tube 3600, a handle body 3700, a threaded actuator shaft 3800, and a deployment knob 3900. In some embodiments, the inserter tool 3000 is coupled to the tissue anchoring device 3100 during manufacturing. In a preferred embodiment, the inserter tool is disposable.

The inserter tool 3000 is designed to insert and manipulate a tissue anchoring device, such the tissue anchoring device described above. In some embodiments, the tissue anchoring device is manufactured to be attached to the inserter tool before packaging. In other embodiments, the tissue anchoring device is coupled to the inserter tool shortly prior to insertion. In a basic configuration, the inserter tool is assembled as follows: the inserter tool 3000 is configured such that the inner rod 3500 is disposed within the outer tube 3600. The outer tube is configured to fit against the proximal end of the spreader 3300. The inner rod 3500 extends through outer tube 3600 and is configured to attach to the distal end of the anchor body 3200 via threading on both the distal hole in the anchor body 3200 and threading on the distal end of the inner rod 3500. The proximal end of the outer tube 3600 is connected to a handle 3700 and the inner rod 500 extends through the proximal end of the outer tube 3600 and screws into the threaded actuator shaft 3800. The actuator shaft 3800 extends just past the proximal end of the handle 3700 where it is configured to secure with a deployment knob 3900.

The individual components of the inserter tool 3000 are further described in detail below. The inserter tool 3000 may be used with any embodiment of a tissue anchoring device. For ease of description, in the description that follows, the inserter tool 3000 is described with reference to tissue anchoring device 100.

Figure 15B:
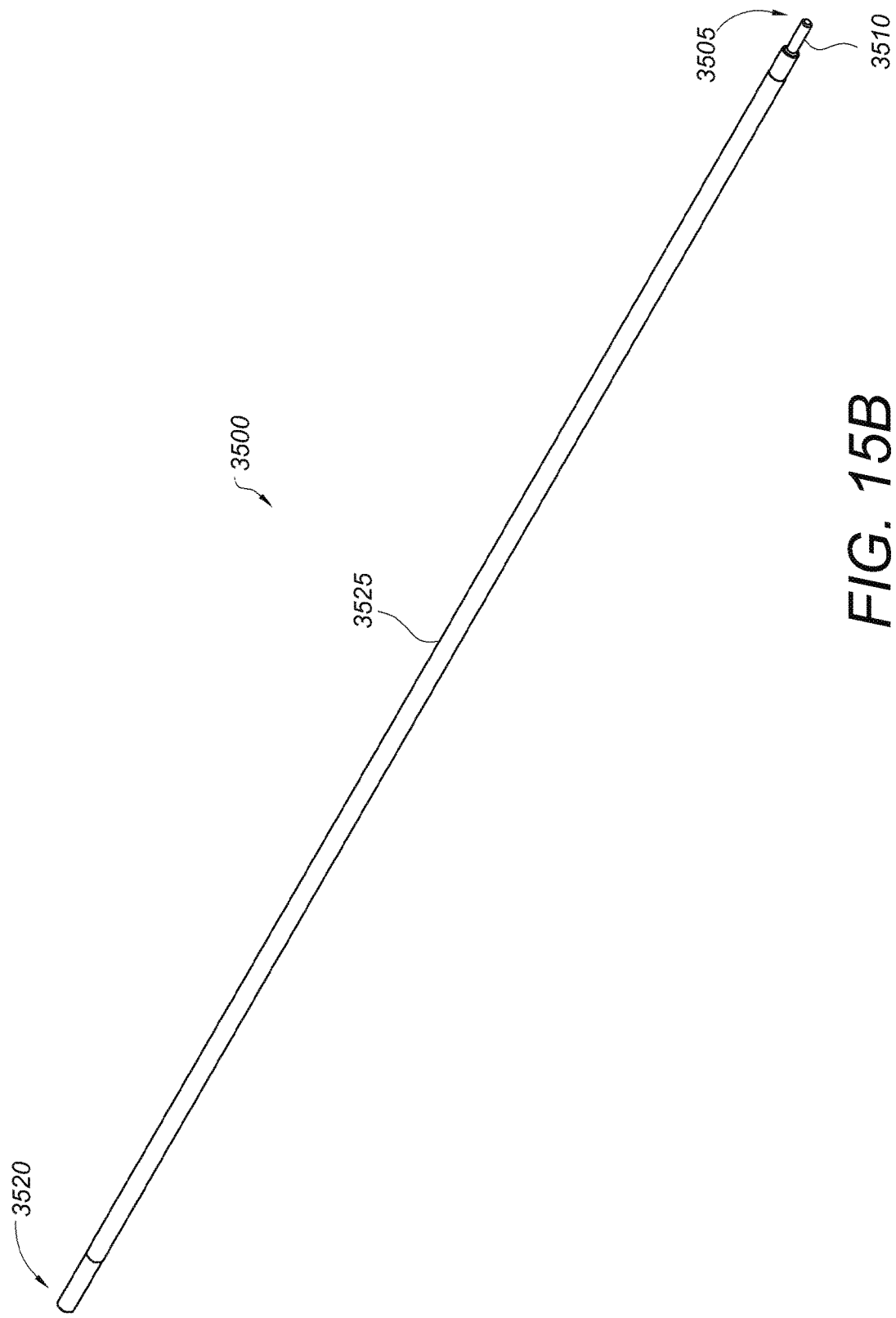
FIG. 15B shows a perspective view of one embodiment of an inner rod component of an insertion tool.

FIG. 15B shows a perspective view of an embodiment of the inner rod 3500. In some embodiments, the inner rod is an inner tube. The inner rod comprises a rod-like or tube-like body 3525, a distal end 3510 configured to secure to a tissue anchoring device spreader 300, and a proximal end 3520 which is configured to interact with the other components of the inserter such as the actuator shaft 3800. The inner rod 3500 is configured such that a proximal end 3520 is advanced through the outer tube 3600 and into the handle 3700 where it is further secured within the actuator shaft 3800 via threading. The distal end of the inner rod 3500 is configured to extend through the central bore in a spreader 300 and an anchor body 200 and then be secured to the distal end of the anchor body 200. Upon activation, the inner rod is retracted until the tissue anchoring device is fully deployed and the inner rod is separated from the anchor.

The inner rod 3500 extends through the central bore in the spreader 300 and the anchor body 200 before coupling with the distal end of the anchor body 200. In one embodiment, the inner rod 3500 couples with the anchor body 200 through threads 3505 on the end of the inner rod 3500 and within the distal end of the anchor body 200. In other embodiments, the inner rod 3500 may couple to the anchor body 200 through other securing mechanisms such as adhesives, welding or frictional fit.

Figure 15C:
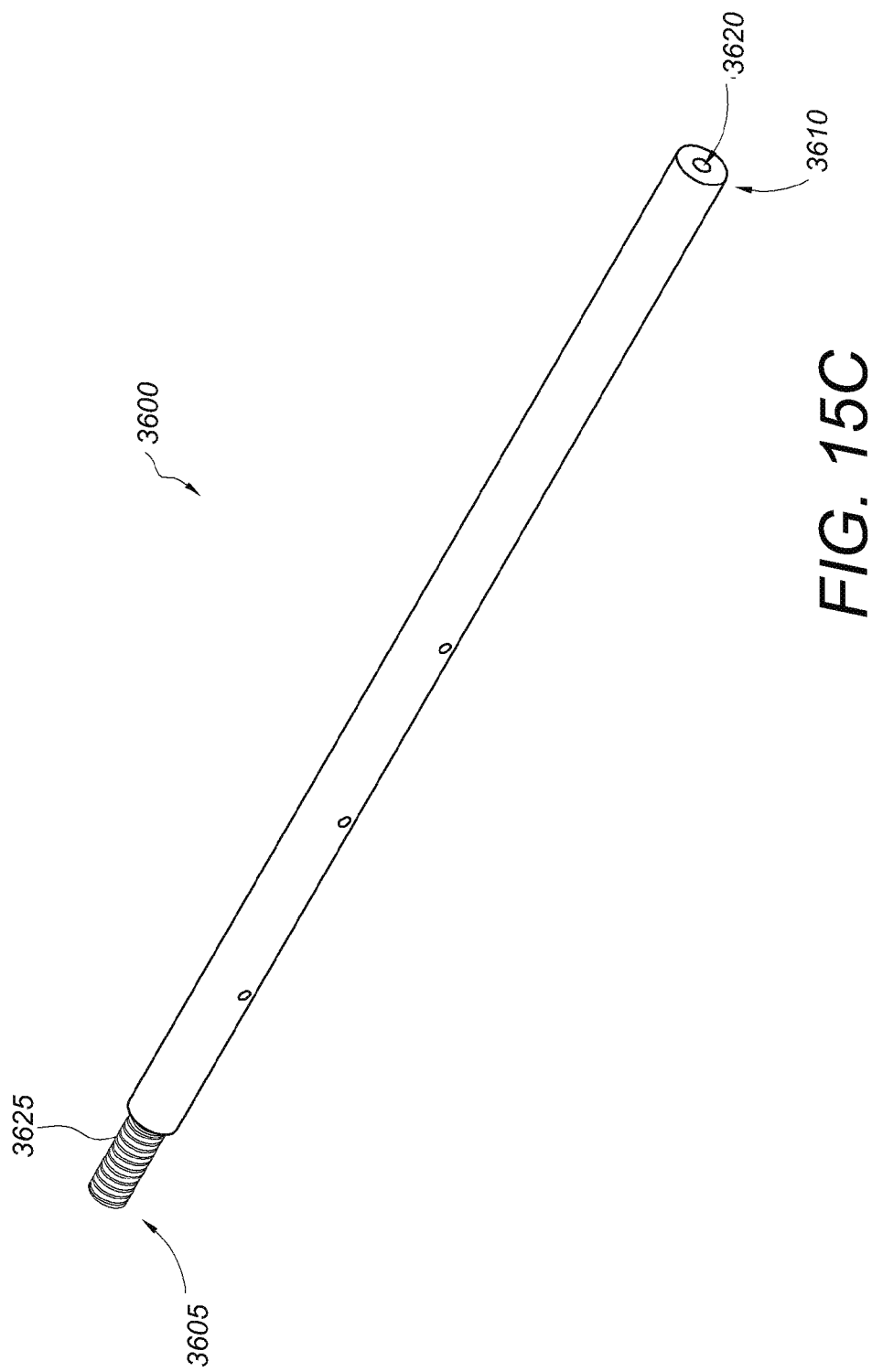
FIG. 15C shows a perspective view of one embodiment of an outer tube component of an insertion tool.

FIG. 15C shows an embodiment of the outer tube 3600. The outer tube 3600 is attached at its proximal end 3605 to the distal end of handle 3700 via threading 3625. The distal end 3610 of the outer tube 3600 is configured such that the inner rod 3500 can be drawn into the outer tube 3600 through the distal end 3610 of outer tube 3600. When the inner tube 3500 is advanced far enough that the spreader 300 locks into place or cannot advance anymore, the distal surface of the outer tube 3600 may be level with the proximal surface of the anchor body 200. When the inner rod 3500 withdraws further into the outer tube upon the continued rotation of the deployment knob and advancement of the actuator shaft, the inner rod 3500 strips the threading from the anchor body 200 and the inserter tool 3000 detaches from the tissue anchoring device 100.

Figure 15D:
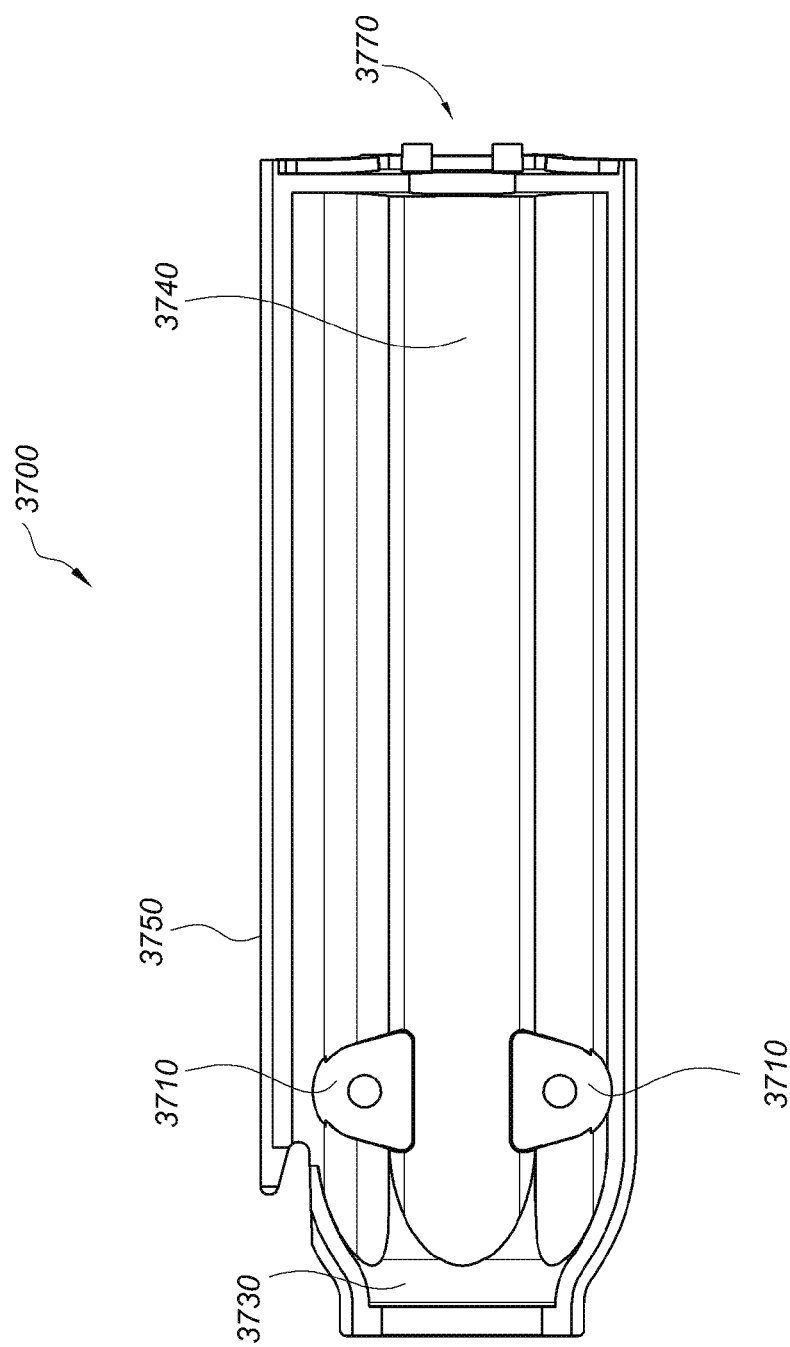
FIG. 15D shows a side view of one embodiment of a handle component of an insertion tool.
Figure 15E:
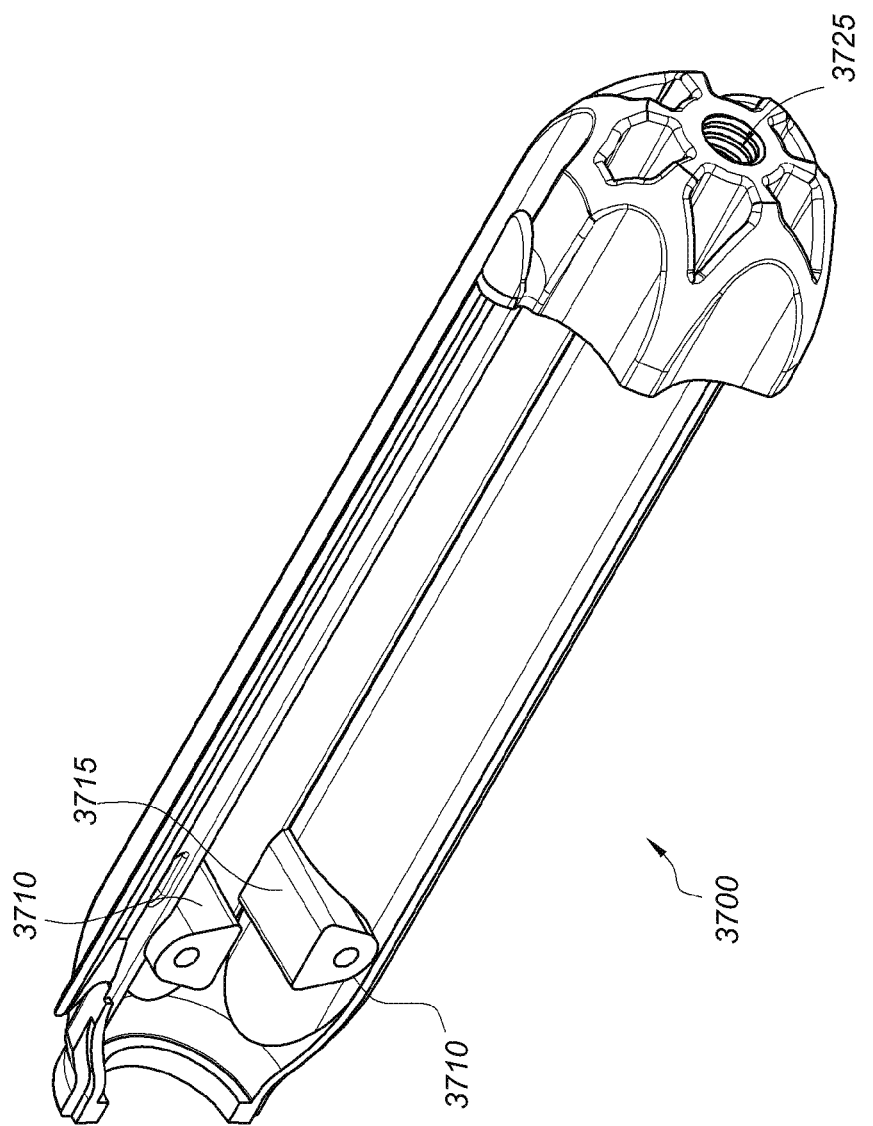
FIG. 15E shows a perspective view of one embodiment of a handle component of an insertion tool.

FIGS. 15D and 15E show embodiments of a handle body 3700. FIG. 15D is a cross-sectional view of one embodiment of a handle 3700 and 15E is a cut-away view of the handle body 3700. The proximal end of the handle 3700 is configured to receive the deployment knob 3900 via the ridges 3730 which hold the knob 3900 secure. The actuator shaft 3800 is housed within the handle body 3700. A set of brackets or braces 3710 each having a flat surface 3715 secure the actuator shaft 3800 within the handle 3700. The distal end 3770 of the handle is configured to receive the outer tube 3600 via threads 3725 in opening 3740. The outer tube 3600 is permanently affixed to the handle 3700 at its distal end.

FIG. 15F depicts the threaded actuator shaft 3800. The actuator shaft 3800 is comprised of a distal end 3805 comprising a threaded hole 3810 which is configured to receive the inner rod 3500, a second threaded portion 3825 on the body of the shaft configured to advance the inner rod 3500, and a proximal end 3820 configured to secure within the deployment knob 3900. The threading 3825 of the actuator 3800 has two flat areas 3830, one on each side, where there is no threading. These flat areas 3830 fit within the flat brackets 3710 of the handle such that the actuator 3800 cannot rotate within the handle.

The body of the actuator shaft 3800 is configured with threading 3825 to permit the shaft 3800 to advance the inner tube 3500. The body of the actuator shaft 3800 is not perfectly round, but rather is oval shaped with flat sides 3830 that fit into the handle body 3700 in such a way that the actuator shaft 3800 cannot itself rotate when the deployment knob 3900 is turned and the shaft 3800 advances via knob 3900. Thus, the threads do not go all the way around the shaft but rather flatten out on the flattened sides of the shaft. The actuator shaft is configured as a coaxial system. That is, the spreader 3300, inner tube 3500 and actuator 3800 are configured to operate as one piece. The flat brackets 3710 in the handle make the actuator shaft 3800 stay on plane such that the actuator shaft 3800 itself cannot rotate within the handle 3700. The proximal end of the inner tube 3500 couples with the distal end of the actuator shaft 3800 via threading.

Figure 15G:
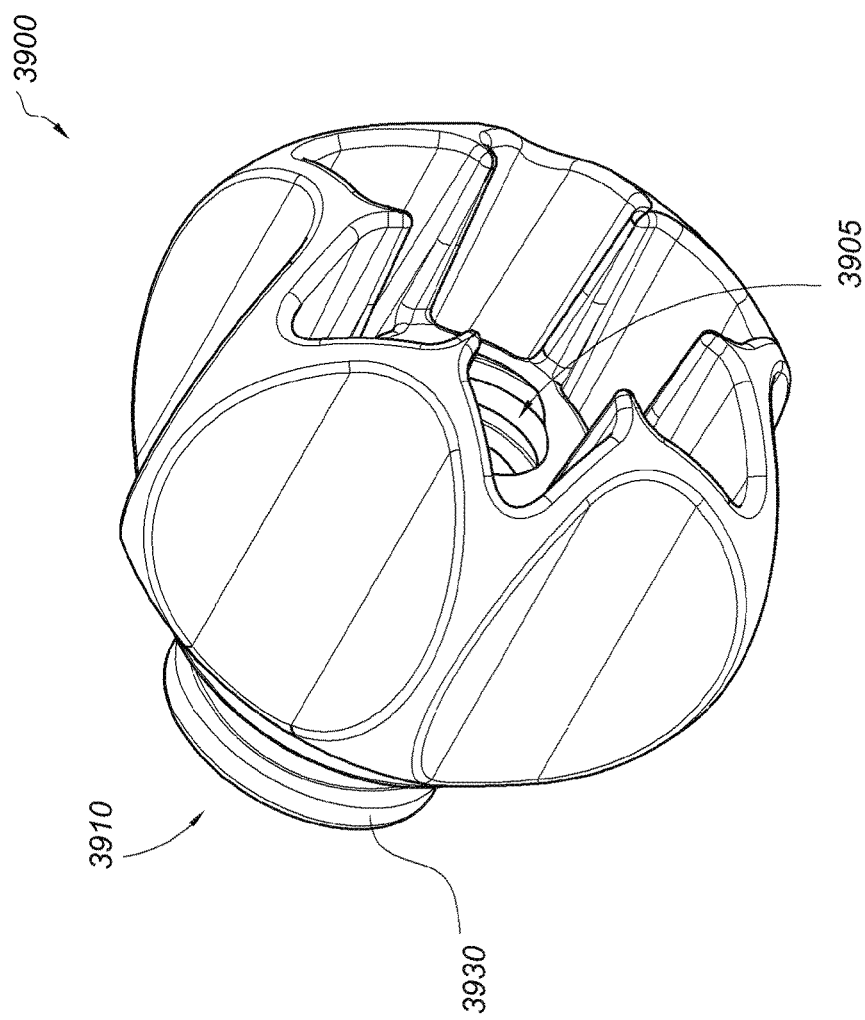
FIG. 15G shows a perspective view of one embodiment of a deployment knob component of an insertion tool.

FIG. 15G depicts a deployment knob 3900. The deployment knob 3900 comprises a central hole 3910 which is configured with threading 3905, and a groove 3930 configured to be received by a corresponding ridge 3730 of the handle 3700. The threading 3905 in the central hole 3910 is configured to receive the actuator shaft 3800. The deployment knob 3900 is configured to advance, relative to the deployment knob 3900, the inner rod 3500 via the actuator shaft 3800. The actuator shaft 3800 is joined at its proximal end to the distal end of the deployment knob 3900 via threading 3905 in the central hole 3910. The actuator shaft 3800 is attached to the inner rod 3500 by way of the proximal end of the inner rod 3500 advancing into the distal end of the actuator shaft via threading so that when the deployment knob 3900 is rotated, the mechanism of the shaft 3800 advances the inner rod 3500 proximally such that the spreader 300 is then advanced into the anchor body 200 to expand the anchor body 200 into bone and secure the tissue anchoring device 100.

In one embodiment, the deployment knob 3900 is threaded 3905 to receive the actuator shaft via the groove 3930 of knob 3900 fitting with the proximal end ridge 3730 of the handle body 3700. As the deployment handle is turned, the actuator shaft 3800 is advanced in a proximal direction until the anchor body 200 is deployed and locked into place.

When in the position for deployment, the inner rod 3500 is positioned within the outer tube 3600, and the outer tube is flush with the anchor body 200. The inner rod 3500 may hold the anchor body 200 steady during insertion and deployment. The inner rod 3500 extends through the spreader 300 and couples to the anchor body 200 via threading. The spreader 300 is configured to be advanced distally through the proximal end of the anchor body 200 by the retraction of the inner rod 3500 via rotating the deployment knob 3900, which pulls the anchor body 200 proximally relative to the spreader 300.

The outer tube 3600 provides the mechanism to push the spreader 300 into the central bore 265 in the anchor body 200 to fully expand the anchor body 200. During deployment of the tissue anchoring device, the inner rod 3500 is continually retracted via a screwing motion until the spreader 300 locks into the anchor body 200. As the deployment knob 3900 continues to turn and the inner rod 3500 continues to pull on the threads of the anchor body 200, the inner rod 3500 strips the threads from the inside of the anchor body 200 and the insertion tool 3000 releases from the anchor body 200. Any thread shavings are contained within the outer tube 3600.

In some embodiments, a pre-attached delivery handle is provided. In some embodiments, the insertion tool or delivery handle is disposable. In other embodiments, the insertion tool can be sterilized, reloaded, and reused.

Those of skill in the art will appreciate other inserters and mechanisms that may be used to insert and deploy the tissue securing anchor described herein. Although a particular insertion device for inserting and manipulating a tissue anchoring device has been described, it should be understood that other inserter designs may be used for manipulating the tissue anchoring device described above in order to insert the anchor and soft tissue into bone. For example, it may be possible to use separate tools for inserting the anchor, securing soft tissue, and securing the anchor.

The anchors described above may be used to secure a tissue graft in an ACL repair. In some embodiments, the anchors described above are used to anchor tissue in a bone tunnel in the tibia. In such procedures, the tissue graft is first anchored within a bone tunnel in the femur. Any suitable anchor may be used to secure tissue to the femur. In some embodiments, suitable anchors include a tissue grasping feature that can be used to capture tissue and feed it through bone tunnels in the tibia and/or femur. In some embodiments, the tissue grasping feature includes a suture loop that can be tightened around one or more strands of tissue.

Figure 16A:
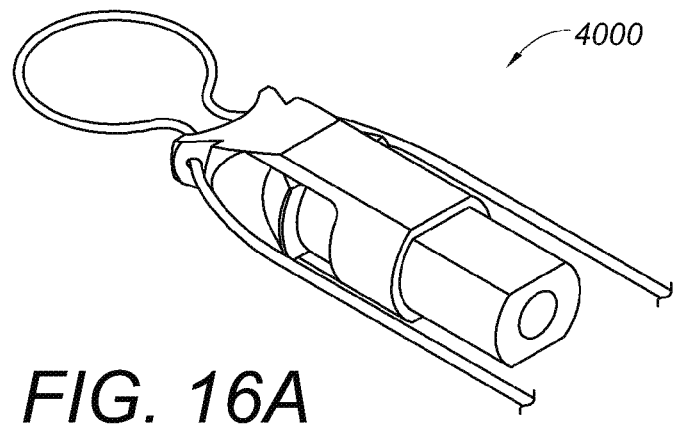
FIG. 16A shows a perspective view of one embodiment of a femoral tissue capture anchor device in an undeployed or unexpanded state.
Figure 16B:
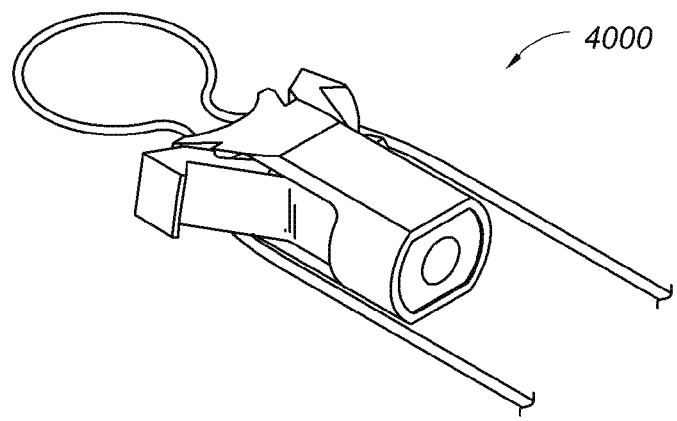
FIG. 16B shows a perspective view of one embodiment of a femoral tissue capture anchor device in a deployed or expanded state.

One example of such a suture loop anchor 4000 is depicted in FIGS. 16A and 16B and described in more detail in FIGS. 13A-16B in U.S. Patent Application Publication No. 2011-0112550, which is incorporated herein by reference in its entirety. FIG. 16A depicts the femoral anchor 4000 in an undeployed state with suture loop ready to capture tissue. After tissue capture and insertion in the femur, lateral protrusions on the anchor 4000 may be deployed to secure the anchor and issue into the femur. FIG. 16B depicts the femoral anchor 4000 in its deployed state.

In other embodiments, a modified version of the tibial anchor described above may be used as the femoral anchor. One such embodiment of a femoral anchor 5000 is depicted in FIG. 17. In this case, instead of a rounded distal end, the anchor body 5100 comprises a flat, depressed, or saddle shaped distal end 5106. Two apertures or provided in the distal end 5106 to accommodate the treading of a suture to form a suture loop 5200 in the distal end. As in the anchor described in FIGS. 16A and 16B, tissue may be captured within the suture loop 5200, the suture tightened, and then the anchor 5000 with captured tissue inserted into the femoral bone tunnel. The anchor 5000 may be deployed using the same spreader and inserter as described above for the tibial anchor.

Those of skill in the art will appreciate other suitable femoral anchors for use in combination with the tibial anchor described herein in performing a torn ACL repair.

FIGS. 18A-18D depict some non-limiting suitable ACL repair techniques utilizing the anchors described herein. First, as depicted in FIG. 18A, a bone tunnels 6100 and 6200 are formed in the tibia and femur, respectively. In some embodiments, both tunnels 6100 and 6200 are formed using a single drill drilling through the tibia and then into the femur. In other embodiments, the femoral tunnel 6200 and tibial tunnel 6100 may be formed separately. Next, a surgeon obtains a suitable tissue graft 6300, which may include tendon from the patient (e.g., one or more patellar or hamstring tendons), from a cadaver, or a synthetic graft. The tissue graft 6300 is then captured by a femoral anchor 1100, such as, for example, any of the anchors 4000, 5000 described in FIGS. 16A-17. The femoral anchor 4000 (as an example) is then inserted into the femoral tunnel 6200 and deployed to secure the graft 6300 into the femur.

In one embodiment, as depicted in FIG. 18B, a lateral technique is used whereby the surgeon inserts the femoral anchor 4000 with captured tissue graft 6300 laterally into the space between the femur and tibia. The femoral anchor 4000 is then inserted directly into the femoral bone tunnel 6200. The joint may be abducted to facilitate direct insertion in the femoral tunnel 6200. After insertion of the femoral anchor 4000, the tissue graft 6300 may then be fed down through the tibial bone tunnel 6100 and out the other side resulting in the configuration depicted in FIG. 18C. In one technique, a suture loop is fed up through the tibial tunnel 6100, the graft 6300 is fed through the loop, and then the loop is pulled back through the tibial tunnel 6100, drawing the graft 6300 with it.

In an alternative embodiment, an in-line approach may be used where the femoral anchor 4000 with captured tissue graft 6300 is inserted through the tibial bone tunnel 6100 and then into the femoral bone tunnel 6200. The result is graft 6300 running from the femoral anchor 4000 through and out of the tibial tunnel 6100 as depicted in FIG. 18C.

After achieving the configuration of FIG. 18C, the joint may be positioned and the tissue graft 6300 tensioned as appropriate. Next, as depicted in FIG. 18D, a tibial anchor (for example, tibial anchor 100) as described herein may be inserted into the opening of the tibial bone tunnel 6100 and deployed to secure the graft 6300 to the tibia. Excess graft 6300 may then be trimmed to be flush with the tibial anchor 100. As shown in FIG. 18D, in some embodiments, the tibial anchor 100 is configured to extend substantially the length of the tibial bone tunnel 6100. In some embodiments of the tissue anchoring device 100 disclosed herein, expansion of the tibial anchor 100 is relatively uniform. In other embodiments, the tissue anchoring device is configured to expand at various locations along the length of the tibial anchor 100. Thus, the use of any of the above-described tibial anchors for ACL repair procedures may advantageously allow for fixation of the tissue to bone throughout the length of the tibial bone tunnel 6100. In various embodiments, the length of the anchor is greater than about 30 mm, greater than about 35 mm, greater than about 40 mm, or about 45 mm.

In one embodiment of a method of ACL repair, the tibial anchor 100 may be inserted into the opening of the tibial bone tunnel 6100 and pushed through distally until at least a distal tip of the tibial anchor 100 emerges on the other side of the tibial bone tunnel 6100. In such embodiments, the tibial anchor 100 is then pulled proximally back until the distal tip of the tibial anchor 100 is no longer visible. Such an insertion mechanism ensures the tibial anchor 100 is properly sized and placed in the bone tunnel such that the tibial anchor 100 extends substantially the length of the tibial bone tunnel 6100. In some embodiments, such placement will allow for aperture fixation of the tibial anchor 100 at both a distal opening and a proximal opening of the tibial bone tunnel 6100.

Additionally or alternatively, in one embodiment of a method of ACL repair, the tibial bone tunnel 6100 is measured to determine its length. In some such embodiments, a measurement tool or guide is inserted into the tibial bone tunnel 6100 after formation. The length of the bone tunnel 6100 is detected, and an appropriately-sized tibial anchor (for example, tibial anchor 100) is selected to fit substantially the entire length of the bone tunnel 6100. The anchors and tissue are then inserted in accordance with the methods described in relation to FIGS. 18B-18D. In some such embodiments, an anchor having a length greater than 25 mm is selected. In some embodiments, an anchor having a length of approximately 30 mm, 45 mm, 50 mm, or any value therebetween is selected.

Advantageously, aperture fixation at both a distal opening and a proximal opening of the tibial bone tunnel 6100 may allow for engagement of the tibial anchor 100 (and consequently, the tissue 6300) with both cancellous bone and cortical bone at both ends of the tibial anchor 100. Fixation within the softer outer bone portion of the tibia may lead to better bone growth around the anchor 100 and the tissue, ensuring a secure connection at both ends. In some embodiments, aperture fixation of the tibial anchor at both the distal and proximal sides helps minimize wear on, and irritation of, the tissue 6300; it may reduce the "windshield wiper" effect that can occur when one end of an anchor loosens; and it may also improve the healing process and reduce the risk of anchor failure by increasing the contact between the tissue 6300 and the tibial bone.

In some embodiments, the approach described above is conducted using a single strand of tissue graft 6300. In this case, the graft 6300 may be captured by the femoral anchor 4000 and doubled over the end of the femoral anchor 4000 such that two parallel portions of the graft 6300 run from the femoral anchor 4000 to the tibial anchor 100. In other embodiments, two strands of tissue graft 6300 may be doubled over the end of the femoral anchor 4000 resulting in four parallel portions of graft 6300 running from the femoral anchor 4000 to the tibial anchor 100.

Although ACL repair techniques have been described herein, it will be appreciated that the anchors described may be used in any number of procedures where a surgeon desires to fix soft tissue to bone.

For purposes of summarizing the disclosure, certain aspects, advantages and features have been described herein. It is to be understood that not necessarily all such advantages may be achieved in accordance with any particular embodiment. Thus, the invention may be embodied or carried out in a manner that achieves or optimizes one advantage or group of advantages as taught herein without necessarily achieving other advantages as may be taught or suggested herein.

While this invention has been described in connection with what are presently considered to be practical embodiments, it will be appreciated by those skilled in the art that various modifications and changes may be made without departing from the scope of the present disclosure. It will also be appreciated by those of skill in the art that parts mixed with one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

While the present disclosure has described certain exemplary embodiments, it is to be understood that the invention is not limited to the disclosed embodiments, but, on the contrary, is intended to cover various modifications and equivalent arrangements included within the scope of the appended claims, and equivalents thereof.

What is claimed is:

1. An expandable bone anchor, comprising:
an anchor body comprising:
a distal tapered anchor tip;
a plurality of first expandable side portions positioned at a proximal end of the anchor body, wherein the first expandable side portions expand by bending outward such that the first expandable side portion extends outward to a greater extent at its proximal portion than at its distal portion; and
a plurality of second expandable side portions positioned distally of the first expandable side portions, wherein the second expandable side portions expand by bending outward such that the second expandable side portion extends outward to a greater extent at its distal portion than at its proximal portion, wherein each of the plurality of first expandable side portions is longitudinally and axially offset from each of the plurality of second expandable side portions, wherein the distal tapered anchor tip begins to taper in the distal direction at a location distal to the plurality of second expandable side portions; and
a spreader configured to advance distally into the anchor body, thereby causing the first and second expandable side portions to expand outward.

2. The anchor of claim 1, wherein the first and second expandable side portions comprise bone-engaging features.

3. The anchor of claim 2, wherein the bone engage features comprise teeth.

4. The anchor of claim 2, wherein the bone engage features comprise ridges.

5. The anchor of claim 1, wherein the first and second expandable side portion is formed by cuts in a side wall of the anchor body.

6. The anchor of claim 1, wherein the spreader comprises at least a portion that is tapered distally.

7. The anchor of claim 1, wherein the spreader has a body with a constant diameter along its length.

8. The anchor of claim 7, wherein the spreader comprises a circumferential ridge positioned over and at or adjacent to a proximal end of the body of the spreader.

9. The anchor of claim 5, wherein the anchor body tapers distally upon substantially its whole length.

10. The anchor of claim 5, wherein the anchor tip has a hemispherical shape.

11. The anchor of claim 5, wherein the anchor tip has a conical shape.

12. The anchor of claim 5, wherein the second expandable side portions comprise a protrusion extending into a central cavity within the anchor body, wherein advancement of the spreader into the central cavity causes the spreader to contact the protrusion, thereby causing the second expandable side portions to expand outward.

* * * * *

UNITED STATES PATENT AND TRADEMARK OFFICE
CERTIFICATE OF CORRECTION

PATENT NO. : 9,925,036 B2  
APPLICATION NO. : 14/774663  
DATED : March 27, 2018  
INVENTOR(S) : Heaven et al.

Page 1 of 1

It is certified that error appears in the above-identified patent and that said Letters Patent is hereby corrected as shown below:

In the Claims

Column 24, Claim 5, Line 10, please insert --each of-- between "wherein" and "the"  
Column 24, Claim 5, Line 11, please add an "s" onto the word "portion"

Signed and Sealed this  
First Day of May, 2018

Andrei Iancu  
*Director of the United States Patent and Trademark Office*